(12) United States Patent
Gopalsami et al.

(10) Patent No.: US 9,086,487 B2
(45) Date of Patent: Jul. 21, 2015

(54) RADAR DETECTION OF RADIATION-INDUCED IONIZATION IN AIR

(75) Inventors: Nachappa Gopalsami, Naperville, IL (US); Alexander Heifetz, Buffalo, IL (US); Hual-Te Chien, Naperville, IL (US); Shaolin Liao, Darien, IL (US); Eugene R. Koehl, Joliet, IL (US); Apostolos C. Raptis, Downers Grove, IL (US)

(73) Assignee: UChicago Argonne, LLC, Chicago, IL (US)

( * ) Notice: Subject to any disclaimer, the term of this patent is extended or adjusted under 35 U.S.C. 154(b) by 797 days.

(21) Appl. No.: 13/422,832

(22) Filed: Mar. 16, 2012

(65) Prior Publication Data
US 2012/0242544 A1   Sep. 27, 2012

Related U.S. Application Data

(60) Provisional application No. 61/453,868, filed on Mar. 17, 2011.

(51) Int. Cl.
| G01S 13/95 | (2006.01) |
| G01S 13/58 | (2006.01) |
| G01N 21/3586 | (2014.01) |
| G01N 21/359 | (2014.01) |
| G01T 7/00 | (2006.01) |
| G01N 21/3581 | (2014.01) |

(52) U.S. Cl.
CPC . G01S 13/95 (2013.01); G01T 7/00 (2013.01); *G01N 21/359* (2013.01); *G01N 21/3581* (2013.01); *G01N 21/3586* (2013.01); *G01S 13/58* (2013.01); *G01S 13/958* (2013.01)

(58) Field of Classification Search
CPC .............. G01S 13/95–13/958; G01N 21/3581; G01N 21/3586; G01N 21/359
USPC ........ 342/26 R, 26 A, 26 B, 26 C, 26 D, 175; 250/341.1
See application file for complete search history.

(56) References Cited

U.S. PATENT DOCUMENTS

| 5,623,145 A * | 4/1997 | Nuss .............................. 250/330 |
| 5,939,721 A * | 8/1999 | Jacobsen et al. .............. 250/330 |
| 6,967,612 B1 * | 11/2005 | Gorman et al. ................. 342/22 |
| 7,495,218 B2 * | 2/2009 | Gopalsami et al. ......... 250/336.1 |

(Continued)

OTHER PUBLICATIONS

"Millimeter-Wave Radar Detection of Chemicals, Gases, and Radiation", Argonne National Laboratory, Cached May 27, 2010, retrieved on Mar. 6, 2015 from The Way Back Machine at http://web.archive.org/web/20100527143602/http://www.ne.anl.gov/capabilities/sinde/factsheets/Profile_MMWave_9-16-04.pdf.*

(Continued)

*Primary Examiner* — Peter Bythrow
(74) *Attorney, Agent, or Firm* — Foley & Lardner LLP

(57) ABSTRACT

A millimeter wave measurement system has been developed for remote detection of airborne nuclear radiation, based on electromagnetic scattering from radiation-induced ionization in air. Specifically, methods of monitoring radiation-induced ionization of air have been investigated, and the ionized air has been identified as a source of millimeter wave radar reflection, which can be utilized to determine the size and strength of a radiation source.

19 Claims, 18 Drawing Sheets

(56) References Cited

U.S. PATENT DOCUMENTS

| | | | |
|---|---|---|---|
| 7,889,113 B2* | 2/2011 | Cardiasmenos et al. | 342/22 |
| 2005/0082479 A1* | 4/2005 | Wallace et al. | 250/330 |
| 2005/0110672 A1* | 5/2005 | Cardiasmenos et al. | 342/27 |
| 2005/0156120 A1* | 7/2005 | Arnone et al. | 250/492.2 |
| 2006/0022140 A1* | 2/2006 | Connelly et al. | 250/338.1 |
| 2006/0255277 A1* | 11/2006 | Cole et al. | 250/341.1 |
| 2007/0263682 A1* | 11/2007 | Zhang et al. | 372/25 |
| 2008/0283761 A1* | 11/2008 | Robinson et al. | 250/370.09 |
| 2009/0146060 A1* | 6/2009 | Farshi | 250/339.06 |
| 2009/0314943 A1* | 12/2009 | Breit et al. | 250/341.1 |
| 2012/0024044 A1* | 2/2012 | Tao et al. | 73/30.01 |
| 2012/0242544 A1* | 9/2012 | Gopalsami et al. | 342/460 |
| 2012/0305773 A1* | 12/2012 | Wu et al. | 250/339.07 |

OTHER PUBLICATIONS

Gopalsami et al., "Millimeter wave detection of nuclear radiation: An alternative detection mechanism," Review of Scientific Instruments, vol. 80, No. 084702, 2009, 4 pages.

Heifetz et al., "Millimeter-wave scattering from neutral and charged water droplets," Journal of Quantitative Spectroscopy & Radiative Transfer, vol. 111, 2010, pp. 2550-2557.

Liao et al., "Microwave Remote Sensing of Ionized Air," IEEE Geoscience and Remote Sensing Letters, vol. 8, No. 4, Jul. 2011, pp. 617-620.

Liao et al., "Nuclear Radiation-Induced Atmospheric Air Breakdown in a Spark Gap," IEEE Transactions on Plasma Science, vol. 40, No. 4, Apr. 2012, pp. 990-994.

* cited by examiner

Decay time: 50-100s

Rise time: 2-3s

RADAR DETECTION OF RADIATION-INDUCED IONIZATION IN AIR

CROSS-REFERENCE TO RELATED APPLICATIONS

This application claims priority from U.S. Provisional Application 61/453,868, filed Mar. 17, 2011, and is incorporated herein by reference in its entirety.

GOVERNMENT INTEREST

The United States Government has rights in this invention pursuant to Contract No. DE-AC02-06CH11357 between the United States Government and the UChicago Argonne, LLC, representing Argonne National Laboratory.

FIELD OF THE INVENTION

This invention relates generally to the field of remote radiation detection. More particularly, this invention relates to systems and methods for remotely detecting radiation via electromagnetic scattering from radiation-induced ionization in air.

BACKGROUND OF THE INVENTION

This section is intended to provide a background or context to the invention that is, inter alia, recited in the claims. The description herein may include concepts that could be pursued, but are not necessarily ones that have been previously conceived or pursued. Therefore, unless otherwise indicated herein, what is described in this section is not prior art to the description and claims in this application and is not admitted to be prior art by inclusion in this section.

Electromagnetic wave remote sensing of earth resources and weather has been studied in the past decades. For example, radar sensing is used in oil and mineral exploration, as well as in monitoring and predicting weather. In addition to these uses, remote detection of nuclear radiation is theoretically possible via electromagnetic wave sensing, because radiation-induced ionization in air increases radar reflectivity. Despite this ionization phenomenon and its associated applications, there has been little research on remote sensing of ionized air.

From a theoretical standpoint, the use of electromagnetic waves in detecting radioactive plumes from nuclear power plant operations has been investigated. Various works have reported radar cross section (RCS) of microwave scattering from charged dielectric spheres. From an experimental standpoint, an X-band Russian radar detected and tracked radioactive plumes from the 1986 Chernobyl accident. As a result of these experiments, the correlation between radioactivity and radar cross section was determined by calibrated measurements. Despite this work, the underlying physics has not been well established; as a result, the scientific community has viewed these results with little confidence. In spite of these initial experimental correlations, it has been found that existing simple plasma models under-predict the RCS by several orders of magnitude. In addition to the lack of understanding surrounding the correlation between radioactivity and radar cross section, current radiation detectors based on air sampling (e.g. ionization counters, scintillators, and semiconductors) are not effective from long distances because of dilution and atmospheric dispersion. Specifically, the limited range of conventional detectors is because of small penetration lengths of alpha and beta particles in air and a decrease of neutrons and gamma rays with the inverse of the square of the distance from the source. Consequently, such systems are limited to a detection range of approximately 100 meters. Thus, although the impact of radiation on electromagnetic waves in air has been generally understood, there is a need for a method and system for utilizing such a relationship without the need for close proximity to the radiation, i.e. a remote detection mechanism.

SUMMARY

The present invention provides a system and method for remotely detecting and monitoring airborne nuclear radiation using millimeter wave technology. It is desirable to overcome the limitations of current radar radiation detection research, which either lacks understanding in the scientific community or is unable to accurately detect radiation. It is also desirable to overcome the limited detection range of conventional detectors.

Various embodiments of the millimeter wave radiation detection system of the present invention may be applied, among other uses, to far-field proliferation detection of nuclear facilities and fuel processing operations, nuclear materials movement, leaks of radioactive materials, and emergency response planning. The system may have meteorological uses, such as aiding in understanding cloud and rain formation and in early monitoring of thunderstorms.

These and other advantages and features of the invention, together with the organization and manner of operation thereof, will become apparent from the following detailed description when taken in conjunction with the accompanying drawings, wherein like elements have like numerals throughout the several drawings described below.

BRIEF DESCRIPTION OF THE DRAWINGS

FIG. 10A is a plot showing the time-dependent change in MMW transmission (T) through mist; FIG. 10B is a plot showing the time-dependent profile of air ionization;

FIG. 11A is a plot of time-dependent change in MMW transmission (T) through humid air; FIG. 11B is a plot of time-dependent profile of air ionization;

FIG. 12A illustrates time-dependent change in MMW reflected power R; FIG. 12B illustrates time-dependent profile of air ionization;

FIG. 13A illustrates time-dependent change in MMW reflected power R; FIG. 13B illustrates time-dependent profile of air ionization;

FIGS. 18a-b are a spectrogram of millimeter wave Doppler frequencies for the X-Ray on (FIG. 18a) and X-Ray off (FIG. 18b) where a Doppler frequency near 500 Hz is observed only when the X-Ray was on

DETAILED DESCRIPTION OF VARIOUS EMBODIMENTS

Whereas microwave radar is known to detect highly dense charged columns of air from lightning, meteors, etc. due to a higher plasma frequency than the incident radar frequency, there have been only limited studies on radar detection of weakly ionized air.

A millimeter wave measurement system has been developed for remote detection of airborne nuclear radiation, based on electromagnetic scattering from radiation-induced ionization in air. Specifically, methods of monitoring radiation-induced ionization of air have been investigated, and the ionized air has been identified as a source of millimeter wave radar reflection, which can be utilized to determine the size and strength of a radiation source.

Atoms consist of relatively large particles comprised of protons and neutrons, orbited by negatively charged electrons. Under normal circumstances, atoms consist of equal numbers of protons and electrons, so the atom is neutrally charged. An ion is any atom or molecule that does not have the normal number of electrons, which means it is not neutrally charged. Ionizing radiation is any form of radiation that has sufficient energy to knock electrons away from atoms, thereby creating ions.

Figure 1:
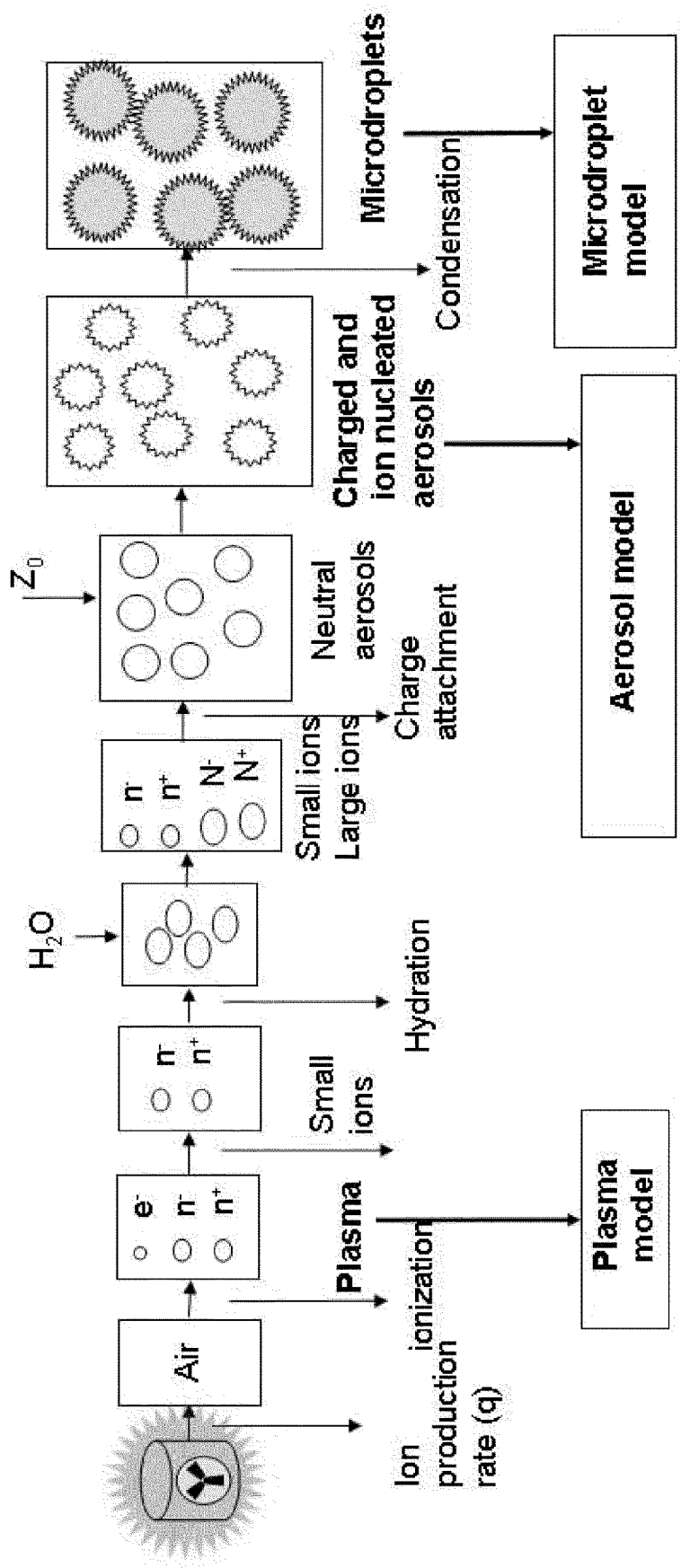
FIG. 1 is a schematic showing radiation-induced ionization of tropospheric air.

Radiation, specifically ionizing radiation, will result in changes to air that is contacted by the radiation. Put differently, the radiation-induced ionization of air consists of a progression of mechanistic steps, from the formation of plasma to molecular aerosols to microdroplet clouds. FIG. 1 illustrates one representation of the resultant changes to air that is exposed to ionizing radiation. The radiation source will emit ionizing radiation as energetic particles or waves, including alpha particles, beta particles, gamma rays, and x-rays. The emitted ionizing radiation will result in an ion production rate (q) in the air that is contacted. The ionization of the air results in the air ionizing into plasma, with free electrons. Specifically, the ionization of air produces $O_2+$ and $N_2+$ with the corresponding "free" $e-$. The free electron attaches quickly (lifetime of 10-6 s) to $O_2$ becoming $O_2-$. Depending on the water content in the air, such as measured by relative humidity, hydration will occur. The hydration with water vapor results in cluster ions such as $O_2-(H_2O)_n$, $NO_3-(H_2O)_n$, $H_3O+(H_2O)_n$, and $NO_2+(H_2O)_n$, where n depends on humidity and can be as much as 20. These are called small and large ions. The ions can charge the neutral aerosols in the air, as well as form ion-nucleated ultrafine aerosols (1-2 nm) in the air. The charge-induced aerosols tend to coagulate and grow to the size of cloud condensation nuclei (100 nm) that activate cloud droplets (10-20 µm). Condensation will occur when a sufficient saturation of the air with water is present. Thus, absent sufficient water in the air, the progression as shown in FIG. 1 will not proceed to formation of microdroplets.

Figure 2:
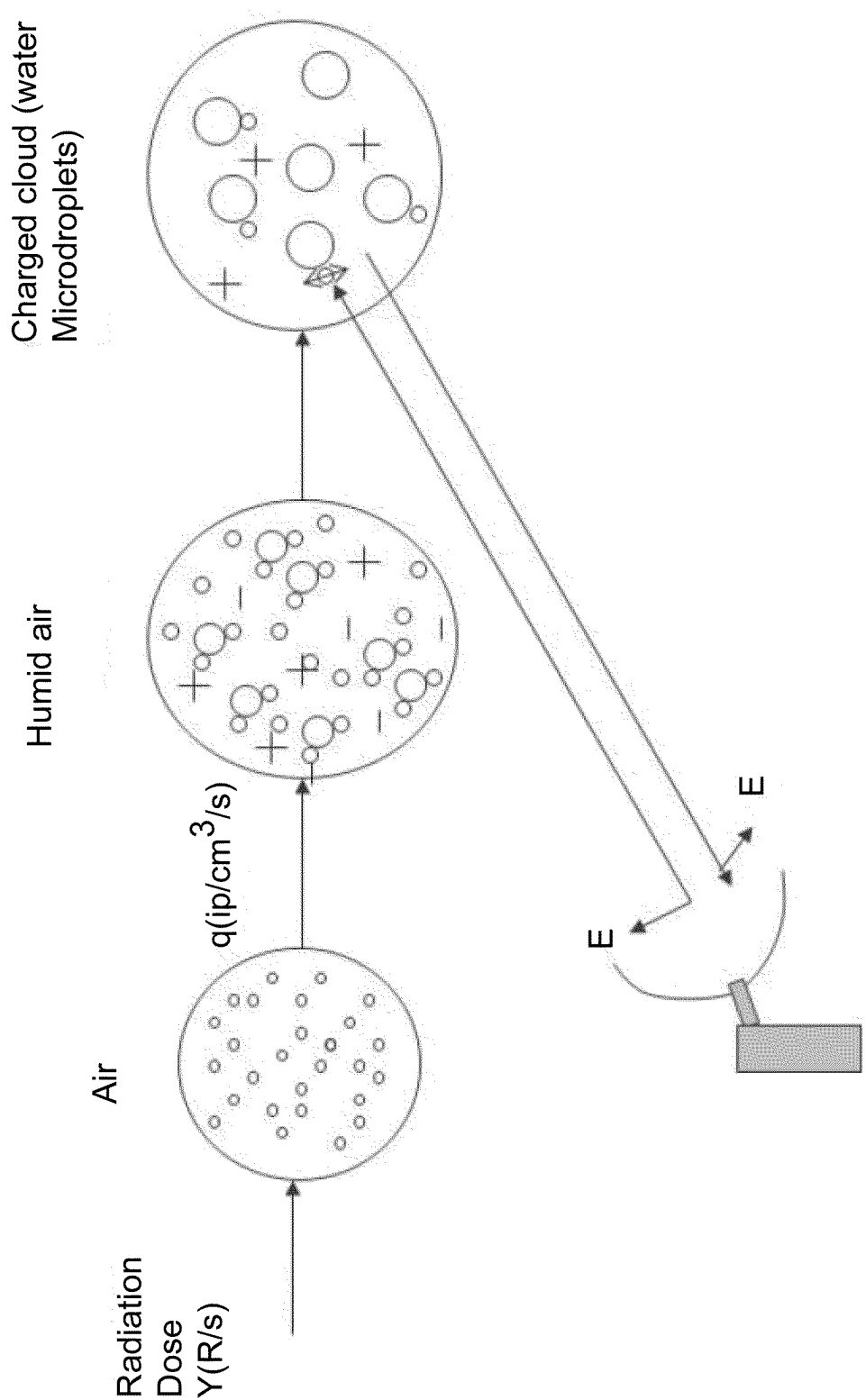
FIG. 2 is an illustration of one possible mechanism by which radiation is detected by its resultant formation of charged water microdroplets.

Phenomenologically, radiation-induced ionization of air can be divided into three models: (1) plasma; (2) aerosol; and (3) droplet. Each of these models provides an opportunity for use in detection of the underlying radiation. Previous work has investigated and estimated the radar cross section of the plasma and droplet models, and suggests that neither model is appropriate for remotely detecting radiation for the following reasons. The plasma model provides measureable radar cross section at radiowave to low microwave frequencies for electron plasma. However, the plasma cloud effects are not sustainable, because free electrons in the air produced by the radioactive sources quickly attach to the $O_2$ molecules. Thus, the use of the plasma model provides an ineffective mechanism by which to detect radiation. The cloud droplet model provides measureable radar cross section. This includes radar cross sections determined using millimeter frequencies, due to the sixth power size dependence on scattering. However, because droplet formation is more likely to occur under supersaturated conditions, the droplet model may not be appropriate for radar detection at low altitudes and is unacceptably dependent on the water content of the air to be monitored Thus, in one embodiment a method of determining the scattering of millimeter waves may be utilized to determine the radiation of a monitored area having a high humidity. FIG. 2 illustrates one such embodiment, where the radiation dose emits radiation to impact a portion of air resulting in ionization of the air as explained above. The ionized air interacts with the water vapor to form a charged cloud, i.e. a collection of associated charged water microdroplets. A millimeter wave emitter directs a millimeter wave at the charged water cloud. A portion of the millimeter waves are reflected back, after having interacted with the charged cloud. The detection of this reflected electromagnetic energy can thus be utilized to determine the underlying radiation's properties that resulted in the detected charged cloud.

Based on the drawbacks of the plasma and droplet models, the ion-cluster aerosol model is most likely to produce enhanced radar scattering of radiation-induced ionization that can be harnessed via a detection scheme to provide information regarding the radiation content of the monitored area. This radiation-induced ionization phenomenon has been investigated both theoretically and experimentally as is further explained below both prophetically and in experimental results.

Figure 3:
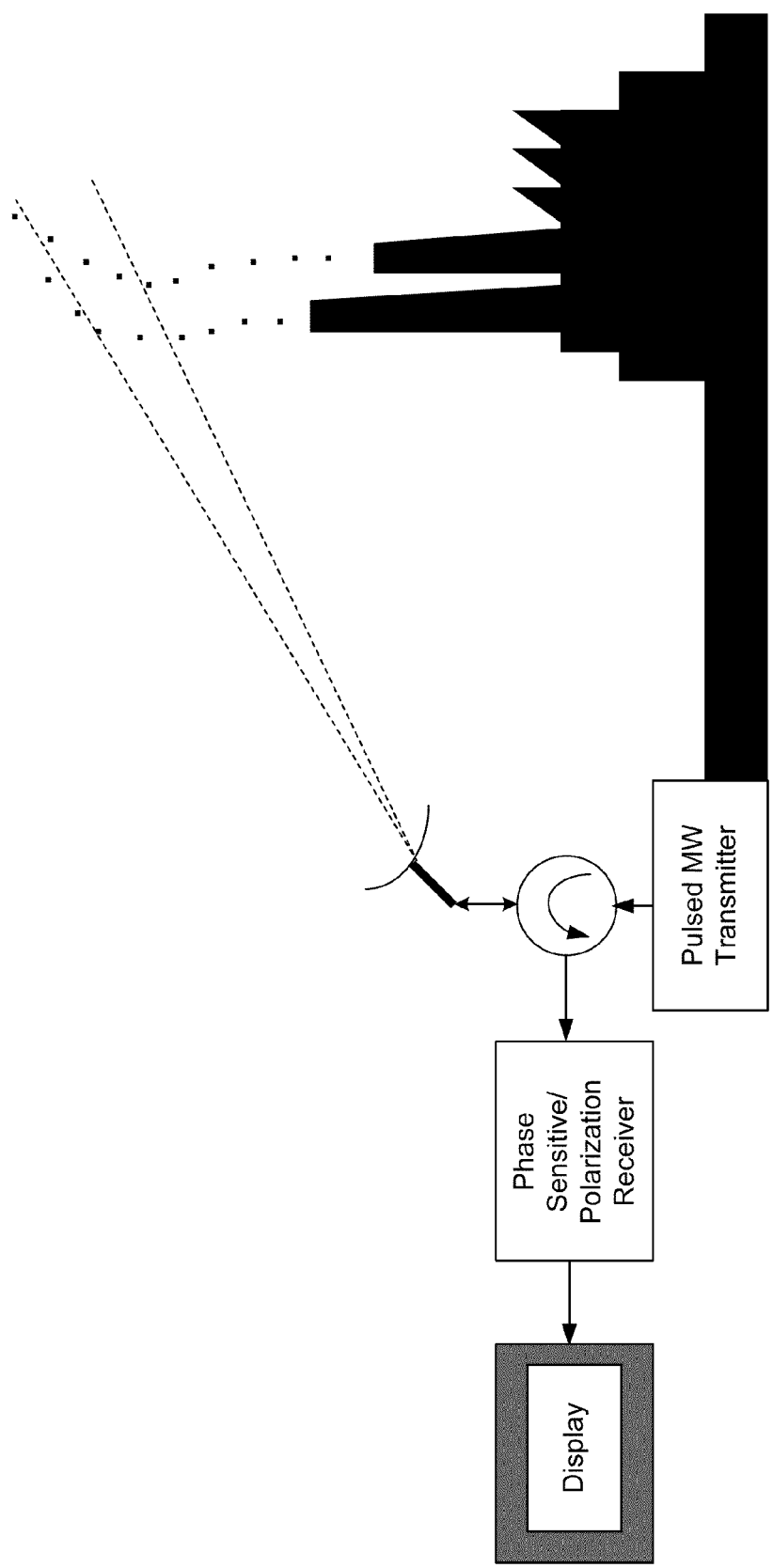
FIG. 3 is a millimeter wave system for detecting radiation-induced ionization of air above a radiation source in accordance with an embodiment of the present invention.
Figure 4:
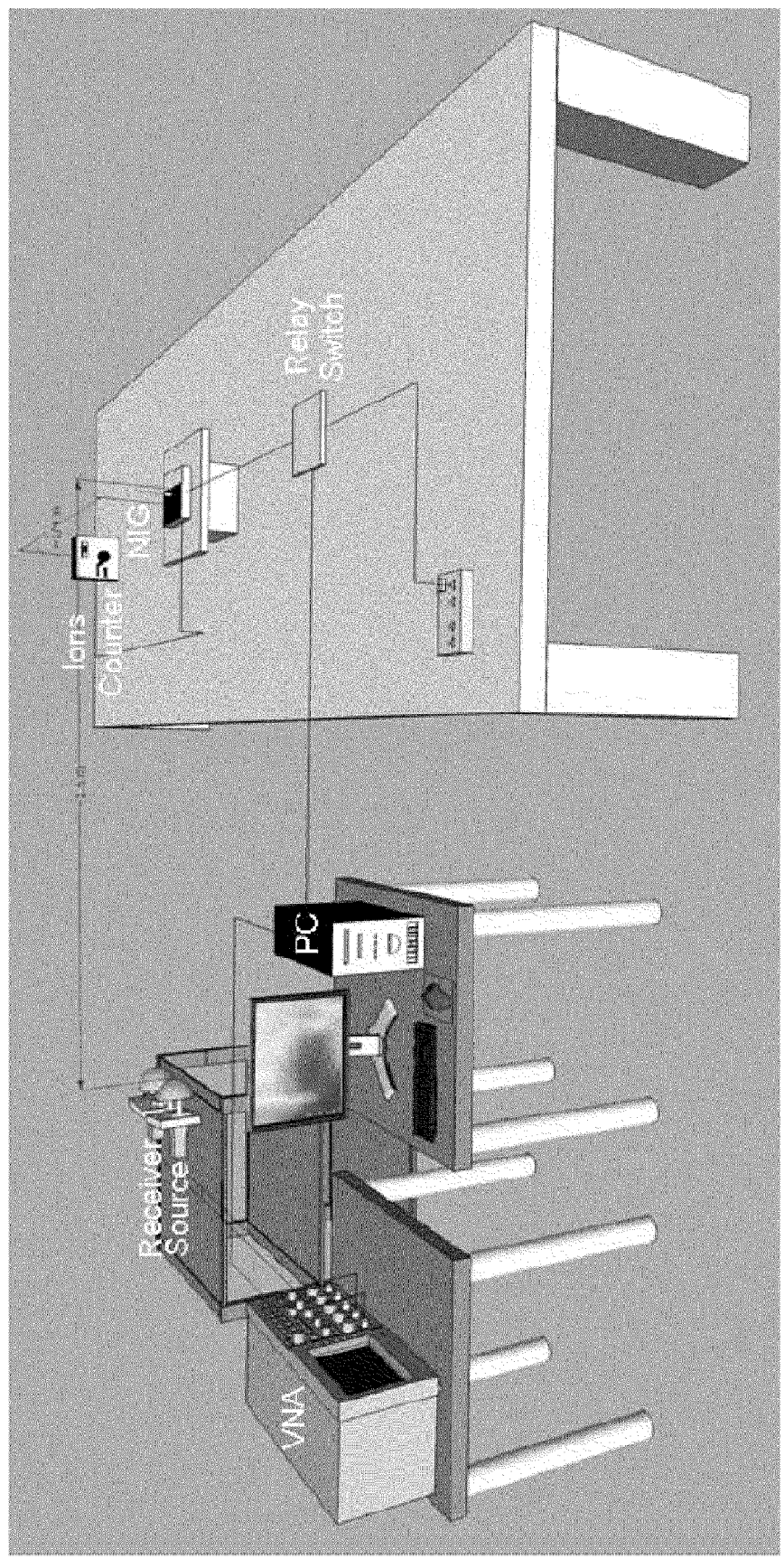
FIG. 4 is a schematic showing an experimental setup for microwave reflection measurement of ionized air.
Figure 5:
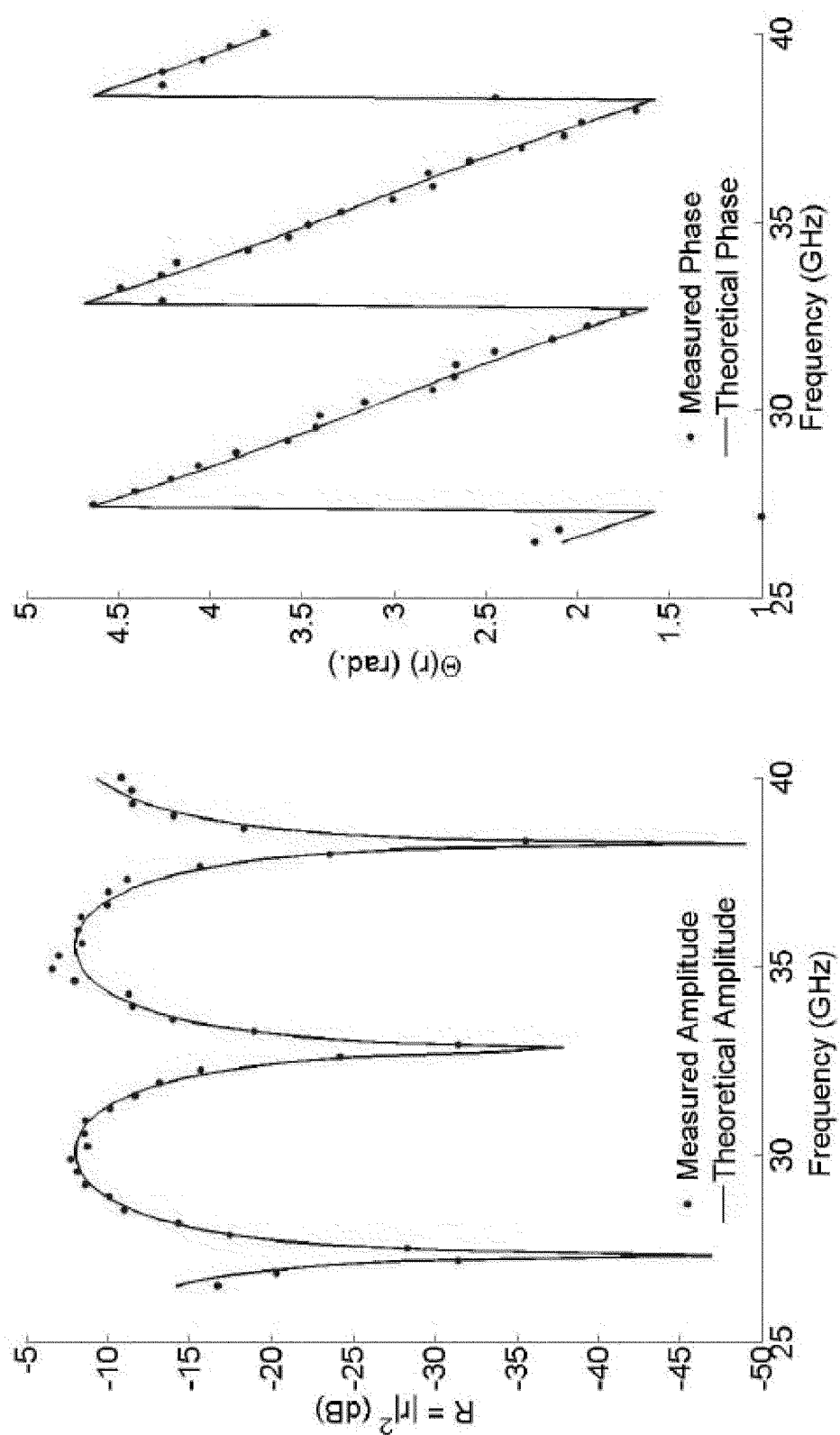
FIG. 5 is a chart of measured amplitude and phase of reflection coefficient for 18 mm thick Teflon slab along with theoretical comparisons.
Figure 6:
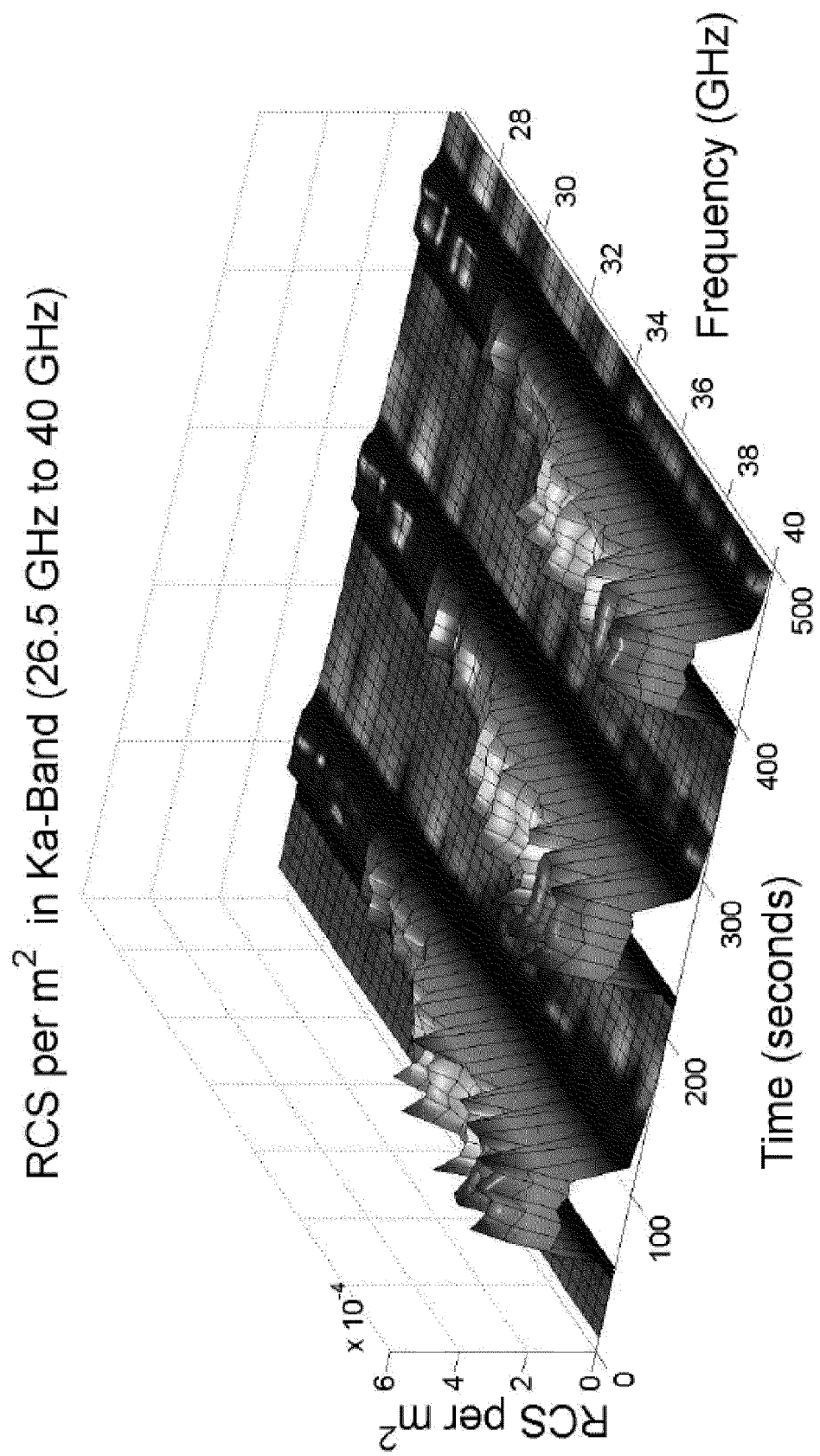
FIG. 6 is a graphical depiction of measured RCS per m2 in the Ka-band (26.5 GHz to 40 GHz) for three NIG-on-off-cycles.

FIG. 3 illustrates one embodiment of a system for detecting the presence of ion-cluster aerosol in a target area. A millimeter wave emitter, such as a pulsed transmitter, directs millimeter waves at a target area, such as the air above an exhaust structure. The reflected radar is detected with a receiver, such as a phase/polarization sensitive receiver.

In one embodiment, the system and methods of the invention may be used to remotely detect and locate nuclear processing facilities, such as those operating covertly. Krypton 85 (85Kr) is released in relatively large quantities (4 mCi/s) during dissolution of spent fuels. Conventional radiation detectors rely upon air sampling, which is not effective from a long range due to dilution and atmospheric dispersion. Use of a system such as illustrated in FIG. 3 provides an indication of ionization of the air around a facility due to the release of the 85Kr.

Modeling and experimental results indicate the strongest mechanistic evidence for radar detection. If millimeter wave radar can provide measurable scattering signals from ionization clouds in air created by radioactive particles and photons, then it would offer a remote detection mechanism. While this technique does not provide radioisotope information, it can determine the location and level of radioactivity from nuclear materials or radioactive plumes. The ability to remotely detect radioactivity via radar would be useful in many areas, including the following: proliferation detection of nuclear facilities and fuel processing operations, nuclear materials movement, leaks of radioactive materials, and emergency response planning.

The ion density in the air due to radioactivity can be calculated using the received data. Ion growth is described by the following second order nonlinear differential equations:

$$q(\text{cm}^{-3}\text{s}^{-1}) = 2.08 * 10^8 * Y(Rs^{-1})$$

$$\frac{dn}{dt} = q - k_{nn}n^2 - k_{nN}nN - k_{nZ}nZ$$

$$\frac{dN}{dt} = k_{nZ}nZ - k_{nN}nN$$

Included in the equations are small ions (n), large ions (N), and neutral particles (Z). FIG. 4 illustrates the ion production rate in air (rise time) and FIG. 5 illustrates the ion decay time in air.

System and methods are described herein that utilize the scattering of MMW from the air containing water which increases when the air is irradiated with negative charges. In one embodiment, the application of these systems and methods is further explained below using a classical electrodynamics model of scattering from a dielectric sphere with diffusion-deposited mobile surface charge. In this model, scattering and extinction cross-sections are calculated for a charged particle with the effective dielectric constant that consists of the volume dielectric function of the neutral sphere, and the surface dielectric function due to the oscillation of the surface charge. The surface dielectric function was obtained from the damped harmonic motion model of an electron. Using the double Debye model of frequency and temperature-dependent permittivity of bulk water as a model of dielectric water sphere. The number of charges was calculated using the model of atmospheric diffusion charging, which estimates the steady-state average number of charges on a water droplet as a linear function of the droplet radius. To calculate the temperature-dependent damping constant, the classical-mechanics model of a linear viscous drag on a particle in water was introduced to the calculations.

Potential applications of this work may include the ability to remotely detect the presence of radioactive gases that are emitted as byproducts of nuclear fuel cycle reactions. Such radionuclides have no distinct spectral lines in the EM spectrum. Atmospheric non-equilibrium cold plasma produced by radioactive decay of unstable isotopes has typical plasma frequency in the kHz band, and it was highly unstable due to recombination and diffusion. On the other hand, the capacitive action of atmospheric fog water droplets to absorb and store charges, provided there was a difference in the scattering properties related to charge, may enable remote detection of radionuclides with MMW. A similar hypothesis was presented in, where formation of a large number of charged atmospheric water clusters following release of nuclear radiation was predicted, but the mechanism of scattering was not presented.

EXAMPLES

Example 1

Microwave Remote Sensing of Ionized Ambient "Room" Air

A schematic drawing of the experimental setup is shown in FIG. 6. A NIG 103 was used to generate ionized air on the order of 1 million negative ions per cubic cm at a distance of about 40 cm away from the Negative Ion Generator ("NIG") needle. The ion density depends on the distance from the NIG needle, which was biased at −18 kV. To perform microwave scattering measurements, Agilent PNA-X series (Model N5245A) Vector Network Analyzer ("VNA") 107 was used to sweep frequency and record the network scattering parameter S21 from 26.5 GHz to 40 GHz (Ka-band). A pair of Ka-band standard gain rectangular horn antennas (Narda® Microwave-East) 109 was used for emission and detection of microwaves. Dielectric lenses 111 were used with each horn antenna to increase the gain of antenna radiation pattern. A computer-controlled relay switch 113 was used to turn the NIG 103 on and off, which allowed for making time-gated transient measurements. The emitter and receiver antennas 109 were placed side by side for bistatic mode detection. The two antennas were separated by a distance of 30 cm to reduce electromagnetic coupling and each was focused at the tip of the NIG needle approximately 1.5 m away. The S21 signal was collected by the VNA and transferred to a Personal Computer (PC) 115 through a GPIB interface. A LabVIEW® Graphics User Interface (GUI) data acquisition program was used to view the experimental observations in real time.

Example 1

System Calibration

The VNA can be calibrated at an arbitrary reference plane in a closed cable system using the Short-Open-Load-Through (SOLT) calibration method. In one experiment, the VNA was used to interrogate an open air space between two antennas, where one must take into account the stray fields due to the coupling of the emitter and receiver antenna signals and the background reflection. Furthermore, the frequency response of the whole measurement system must be known to determine the absolute RCS.

For a plane wave incident upon an infinite dielectric slab of thickness t, the RCS for an incident beam area of $A=\pi a^2$ is related to the Power Reflection Coefficient (PRC) as:

$$RCS = A \times PRC = \frac{AP_r}{P_i} = A\left|\frac{E_r}{E_i}\right|^2 = A|r|^2 = AR, \quad (1)$$

where $P_i$ and $P_r$ are the incident and reflected power and $E_i$ and $E_r$ are the corresponding fields, r and R are voltage and power reflection coefficients. However, due to background field and frequency response of the system stated above, the $S_{21}$ signal measured at the VNA is given by, $$S_{21} = [E_b + E_r]T(f) = E_i[r_b + r]T(f), \quad (2)$$

where $E_i$ is the complex incident plane wave field; $r_b$ is the complex reflection coefficient of the background and r is the reflection coefficient of interest that must be recovered from the signal $S_{21}$; and $T(f)$ is the frequency response of the system. From Eq. (2), the true reflection coefficient was obtained as:

$$r = \frac{S_{21} - S_{21}^b}{E_i T(f)}, \quad (3)$$

where $S_{21}^b$ is the measured background signal when the NIG is off. To obtain $E_i T(f)$, a large piece of metal reflector was placed at the center position of ionized air, which has reflection r=−1 for all frequencies. Let $S_{21}^m$ denote the measurement data from the metal reflector. From Eq. (2), the following results:

$$S_{21}^m = E_i[r_b - 1]T(f), \quad (4)$$

from which the following results:

$$E_i T(f) = S_{21}^b - S_{21}^m. \quad (5)$$

Combining Eq. (3) and Eq. (5), the calibrated reflection coefficient was as follows $$r = \frac{S_{21} - S_{21}^b}{S_{21}^b - S_{21}^m}. \quad (6)$$

From Eqs. (1) and (6), the RCS per m²

$$RCS = \frac{A \times PRC}{A}(m^2) = \left|\frac{S_{21} - S_{21}^b}{S_{21}^m - S_{21}^b}\right|^2 (m^2), \quad (7)$$

and the RCS per volume is given by $$\frac{RCS}{\text{volume}} = \frac{A \times PRC}{A \times t} = \frac{1}{t}\left|\frac{S_{21} - S_{21}^b}{S_{21}^m - S_{21}^b}\right|^2. \quad (8)$$

The calibration procedure may be summarized as follows,
1) make a measurement when NIG is off, denote it as $S_{21}^b$;
2) make another measurement by putting a large piece of metal at the position of the ionized air, denote it as $S_{21}^m$;
3) make ionized air measurement data with NIG turned on and off, denote it as $S_{21}$;
4) perform the RCS calibration as in Eqs. (7) and (8).

Figure 7:
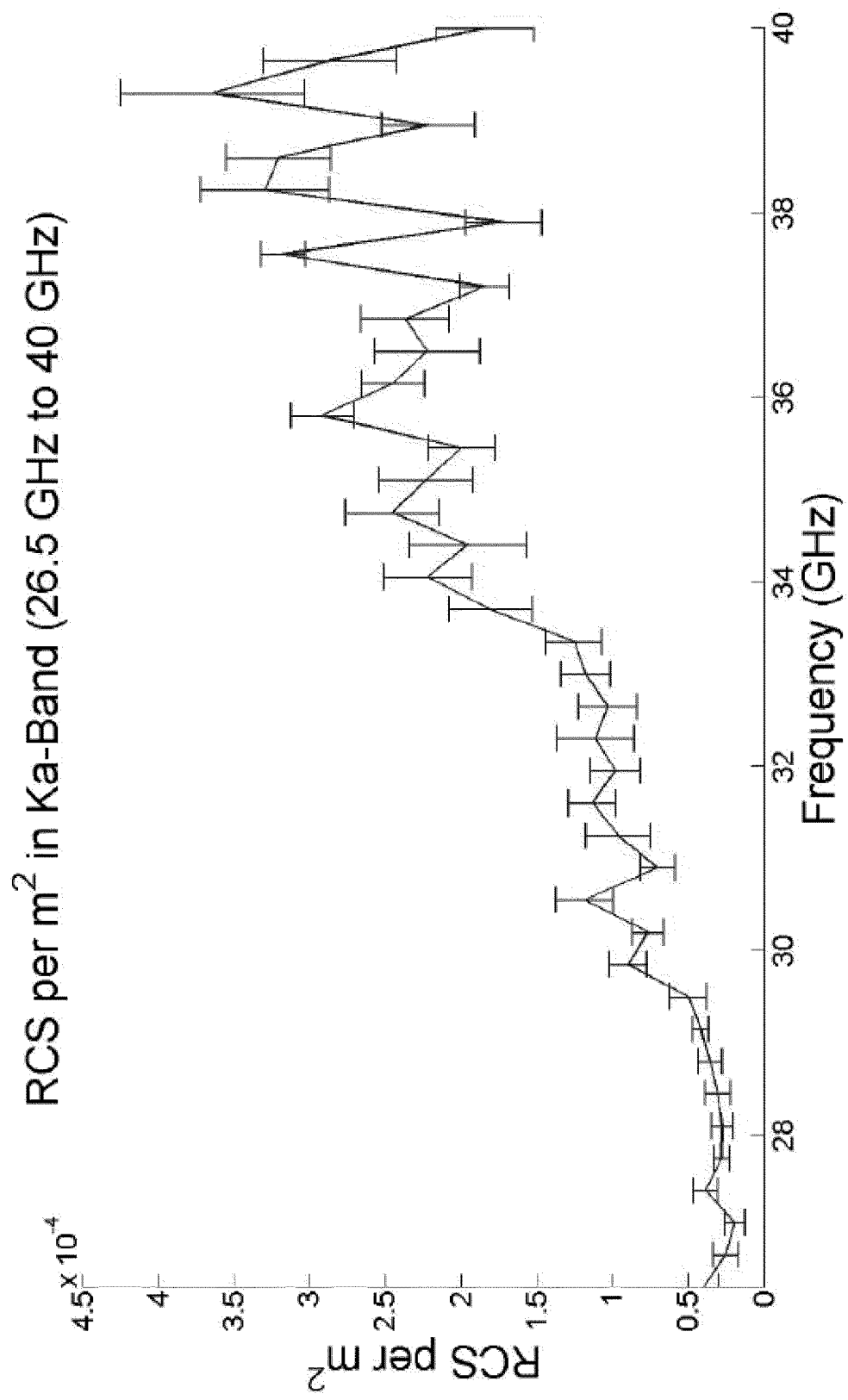
FIG. 7 is a chart of the averaged RCS per m2 in the Ka-band (26.5 GHz to 40 GHz): the error bars show the standard deviation of the RCS per m2.

A calibration was performed on a Teflon slab of thickness t=18 mm and compared it with the theoretical result. For plane wave normal incidence, the reflection coefficient $r_{Teflon}$ is:

$$r_{Teflon} = \frac{\left[\frac{1}{\varepsilon_{Teflon}} - 1\right][1 - \exp(-j2k_{Teflon} t)]}{\left[\frac{1}{\sqrt{\varepsilon_{Teflon}}} + 1\right]^2 - \left[\frac{1}{\sqrt{\varepsilon_{Teflon}}} - 1\right]^2 \exp(-j2k_{Teflon} t)}, \quad (9)$$

where $\varepsilon_{Teflon}$=2.3215 and $k_{Teflon}$ are dielectric constant and wave vector of Teflon, respectively. A good agreement between the theoretical and measured data was obtained as in FIGS. 7A and 7B.

Example 1

Experimental Results

The RCS per m2 obtained from Eq. (7) of the ionized air when NIG was on and off for three cycles. It should be appreciated that the RCS per volume, can be obtained through Eq. (8), with t~¼ m (twice the radius of the ionized air).

Figure 8:
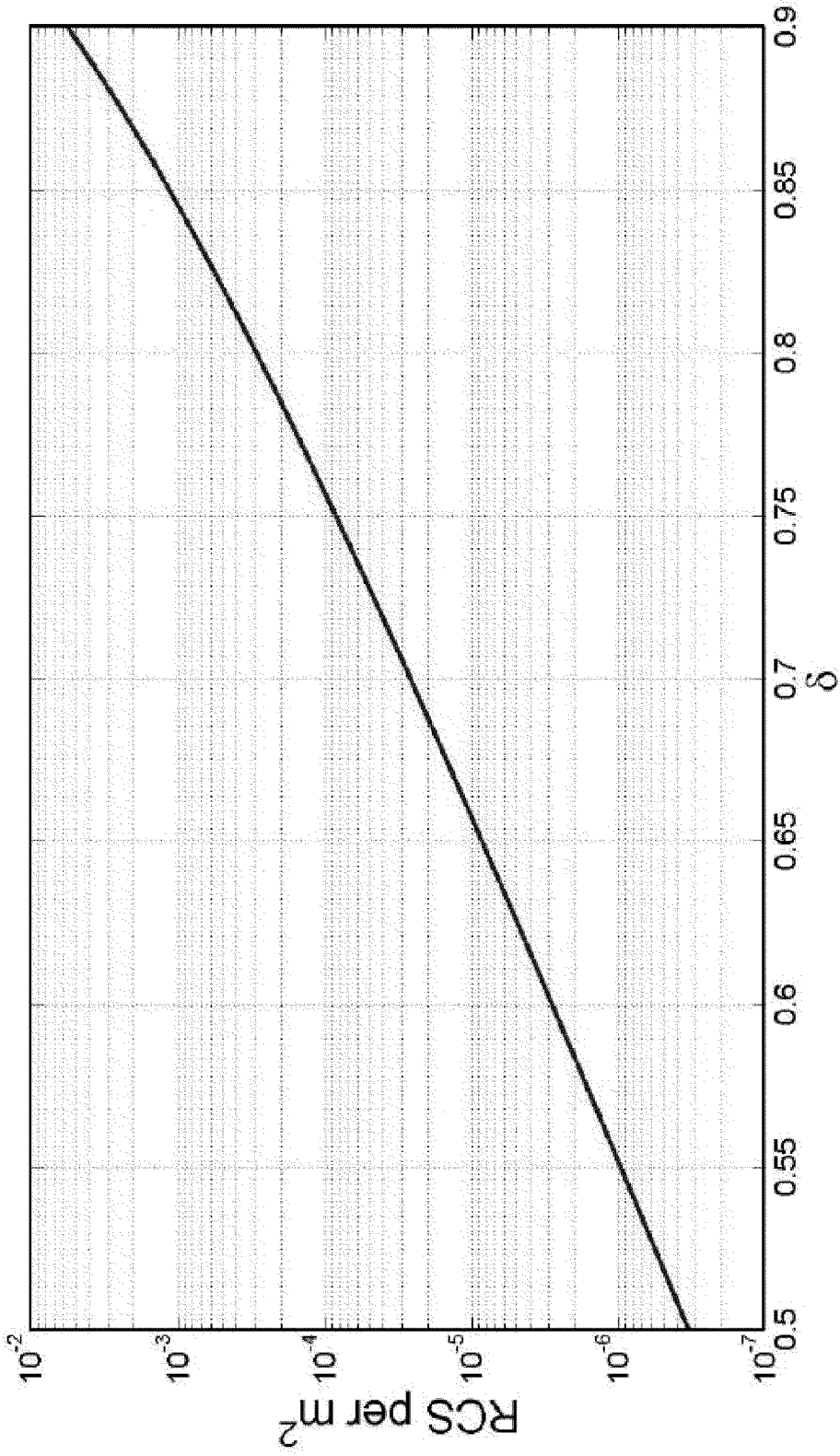
FIG. 8 is a chart depicting the calculated RCS per m2 for an electron density distribution of $10^6 |z|^{-6}$.

The measured RCS per m2 in the Ka-band (26.5 GHz to 40 GHz) is given in FIG. 8 for three NIG-on-off-cycles. When the ionized air was present, the RCS per m2 increases and was on the order of $10^{-5}$-$10^{-4}$ (m2) over the whole band. This level of RCS per m2 can be detected by current radar systems.

Figure 9:
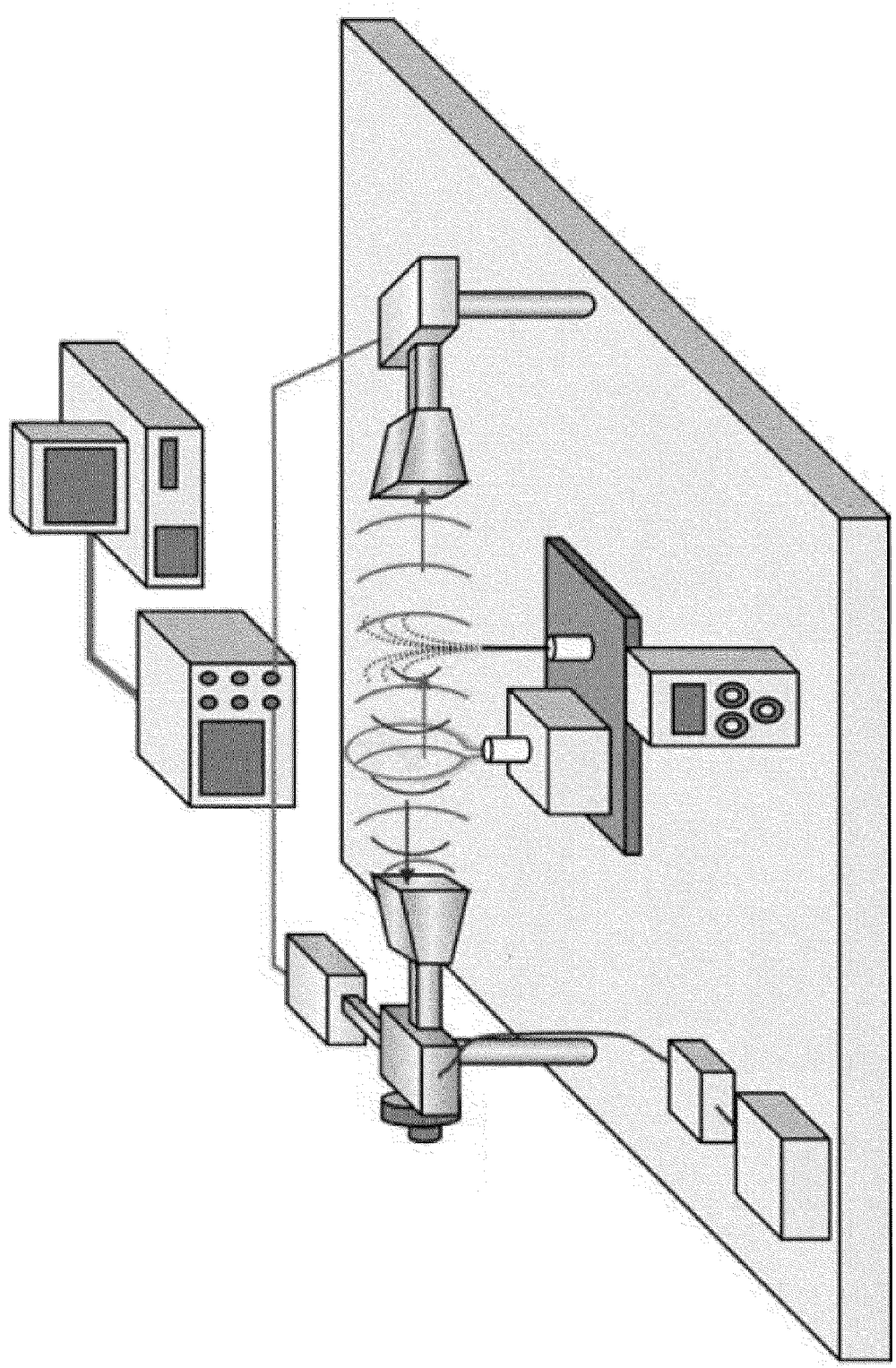
FIG. 9 illustrates another setup used in the described examples relating to the testing of the interaction millimeter waves experience with charged and neutral mist.

Averaging the change of RCS per m2 when the NIG was on from that when the NIG was off for the three NIG-on-off-cycles, the averaged RCS per m2 in Ka-band is shown in FIG. 9.

Example 1

Discussion

Thomson scattering arises from acceleration of free electrons by the incident electric field. The electron density in the ionized air is on the order of, $\bar{n}_e$~$10^6$/cm³ which gives an average spacing between adjacent electrons $d_e$~0.0022 cm, much smaller than the wavelength $\lambda$=1 cm of at a frequency of f=30 GHz. In this case, i.e., within one wavelength scale, the scattered field for a unit plane wave incidence is given by $$\vec{E}_s = s_e \int_V \bar{n}_e(\vec{r})\exp(-j2[\vec{k}_s - \vec{k}_i]\cdot\vec{r})d\vec{r}, \quad (10)$$

where $s_e$ is the single electron scattering strength; $\sigma_T = |s_e|^2 = 6.65\times10^{-29}$ m² is the Thomson scattering of a single electron; $\vec{k}_s$ and $\vec{k}_i$ are scattered and incident wave vectors respectively. The time averaged backscattered RCS for weakly ionized air is given by $$RCS = |\vec{E}_s|^2 = \sigma_T \left|\int_V \bar{n}_e(\vec{r})\exp(-j2[\vec{k}_s - \vec{k}_i]\cdot\vec{r})d\vec{r}\right|^2 \quad (11)$$

Figure 10A:
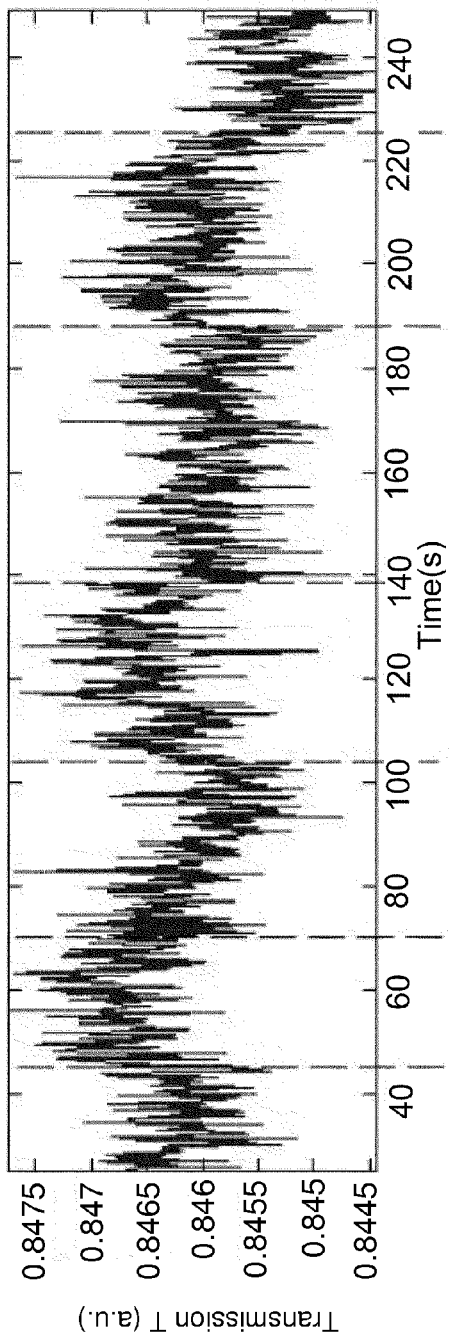
FIGS. 10A-B show a 94 GHz millimeter wave sensing of convective and diffusive mist.
Figure 10B:
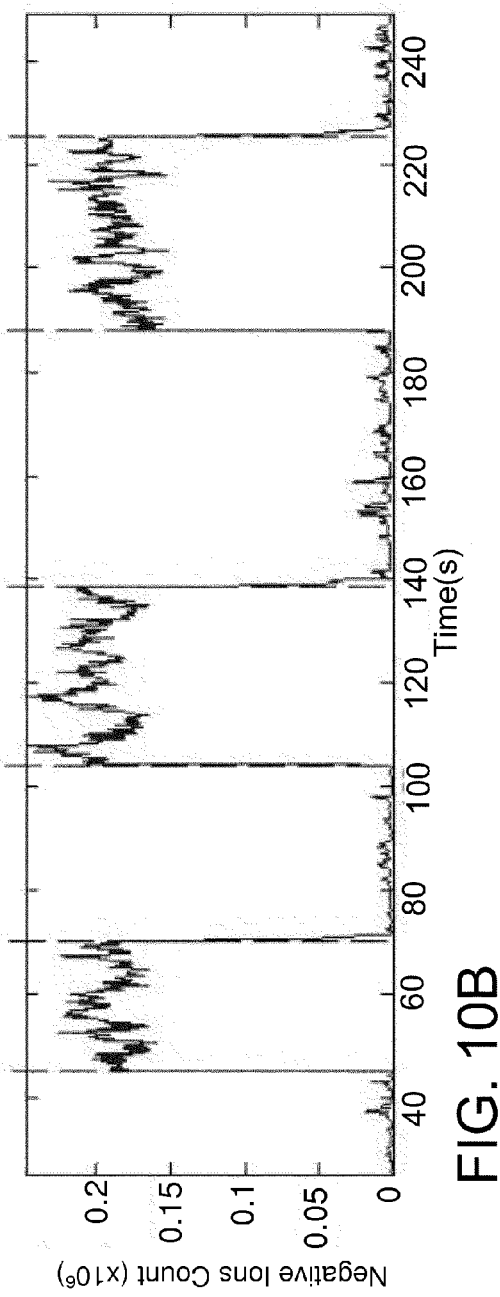

Thus the total scattering depends quadratically on the Fourier transform component of the electron density profile. It is possible to calculate an estimate for the time-averaged backscattering RCS ($|\vec{k}_s - \vec{k}_i|$=2k) for an assumed electron density distribution of $$\bar{n}_e(z) = \bar{n}_e|z|^{-\delta}, \delta\in[0,1) \quad (12)$$

in which case, the RCS becomes $$RCS = \sigma_T[\bar{n}_e]^2 \left| 2^\delta k^{\delta-1} \frac{\sqrt{\pi}\,\Gamma\left(\frac{1-\delta}{2}\right)}{2^\delta \Gamma\left(\frac{\delta}{2}\right)} \right|^2 \text{ m}^2. \tag{13}$$

where $\Gamma$ is the Gamma function. FIG. 10 gives the calculated RCS according to Eq. (13) for different $\delta$, which agrees well with the measured RCS in FIG. 9

Example 1

Conclusion

The observed microwave reflection from ionized air using NIG as the source of ionization RCS on the order of $10^{-5}$-$10^{-4}$ m$^2$ was measured over the whole Ka-band (26.5 GHz to 40 GHz) in room air for a charge density of ~1 million per cm3 at a distance of 40 cm from NIG needles.

Example 2

Millimeter-Wave Scattering from Neutral and Charged Water Droplets

Millimeter wave (MMW) scattering from both charged and uncharged water droplets was investigated. The droplets were produced in the laboratory with an ultrasonic atomizer. Diffusion charging of the droplets was accomplished with a negative ion generator (NIG). Two types of charged droplet experiments were investigated: (1) while an ultrasonic generated mist was flowing across the MMW beam path, the mist was charged with the NIG (the convective approach); and (2) the air was saturated with mist and then charge the humid air with the NIG (the diffusion approach). In the convective approach, charged mist flows away from the MMW beam after the NIG is turned off, so the on and off implies charged versus neutral clearly. In the diffusion approach, which is representative of humid air, water droplets in humid air are diffusively charged; the charges are expected to be neutralized quickly after the NIG is turned off by diffusion and collision with neutral molecules.

Example 2

Experimental Measurements

Figures 11A, 11B:
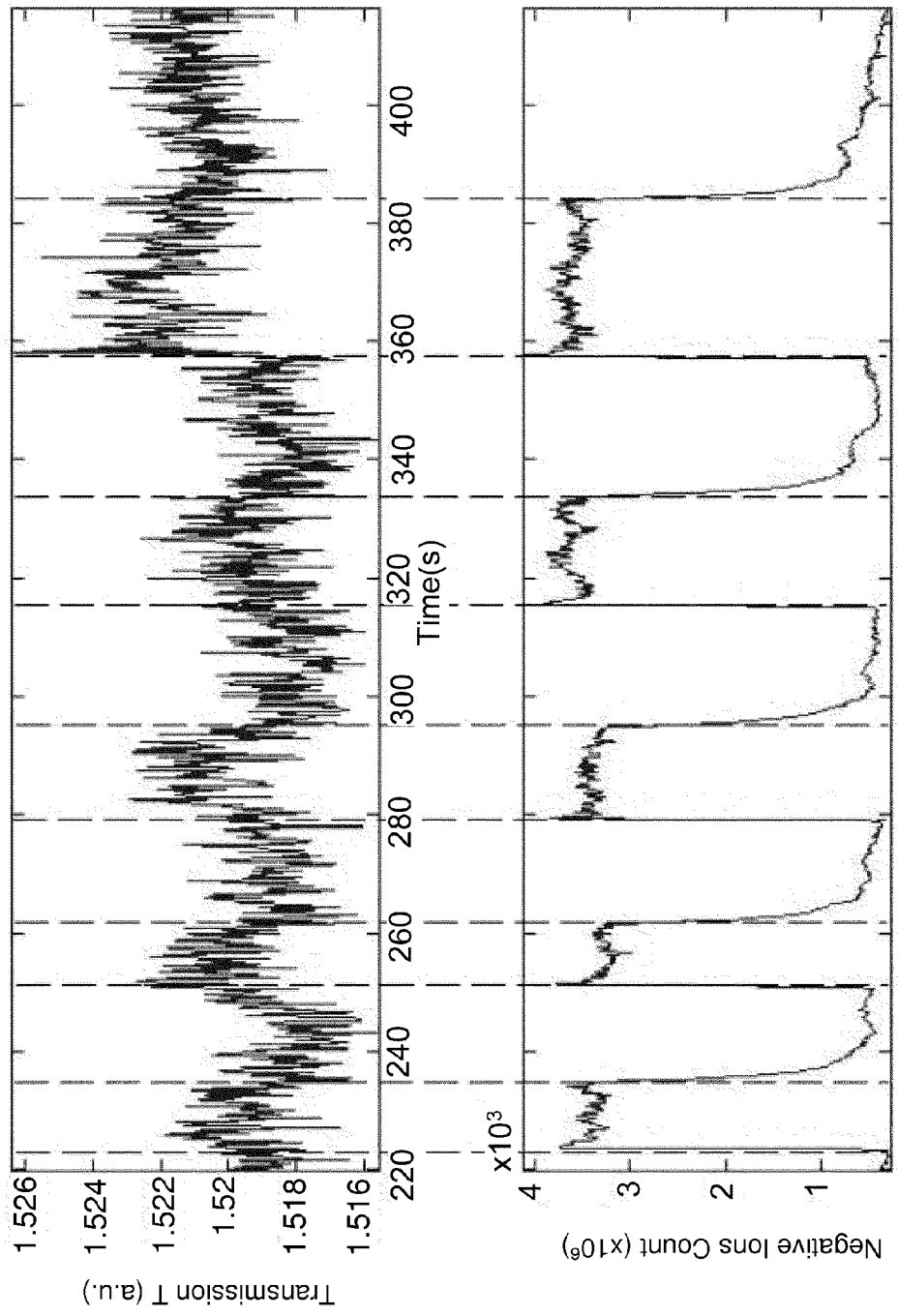
FIGS. 11A-B depict testing of 94 GHz millimeter wave sensing of neutral and charged droplets (the mist was turned on for 30 s and turned off before NIG tests began)

The millimeter-wave transmission and reflection of charged and neutral mists was studied using the setup given in FIG. 11. The millimeter-wave setup consisted of a 94 GHz radiation transmitted and received in open air between a pair of Standard Gain horns. A Gunn diode oscillator was used to generate continuous waves and a pair of Schottky diode detectors was used to measure the transmitted/reflected power. An ultrasonic atomizer (UA) (commercial room humidifier) generated a plume of fine mist in the beam path of millimeter waves. Deionized distilled water was used to produce a neutral mist. The UA produced a room-temperature mist, which eliminated the possibility of MMW scattering due to thermal gradient. The mist was diffusion-charged using a negative ion generator (NIG) by applying a high voltage (−18 kV) in parallel at the tips of several wires pointed in the air. Tips of the NIG wires were placed in the middle of the UA-generated mist. NIG was acting as a cold cathode emitting electrons, which are quickly absorbed by air molecules to form air ions. In the experimental setup the tip of the NIG was in immediate proximity to the mist, thus it is assumed that free electrons were charging the mist.

The 94 GHz millimeter wave transmitter supplies a beam of radiation that scatters neutral and charged water droplets produced by an ultrasonic atomizer. Millimeter wave scattering is monitored with a reflection detector sensor. Millimeter wave transmission through the droplets is monitored with a transmission detector sensor. Both the reflection and transmission sensors convert the physical phenomenon each sensor is monitoring into a measureable electrical signal, such as voltage or current. An oscilloscope displays the electrical signals produced by the reflection and transmission detectors. A data acquisition system (DAQ) converts the analog output signals from the reflection and transmission sensors into a digital signal for processing by a computer. The DAQ includes data acquisition hardware, which primarily acts as the device for digitizing incoming analog signals. The DAQ may also include signal conditioning circuitry in applications where the sensors generate signals that are too difficult or too dangerous to be measured directly with the data acquisition device. The DAQ output is inputted into a computer for processing.

Several experiments were conducted to test the MMW scattering properties of charged versus neutral mist. The experiments were performed for two scenarios: continuously flowing convective and diffusive mist and stationary diffusive-only mist. In the case of the flowing mist, measurements were made while the UA was continuously operating. In the case of the stationary mist, UA would be humidifying the air in the setup for several minutes, but measurements were taken immediately after the UA was turned off. The test scheme for either case consisted of monitoring the change in millimeter-wave transmitted and reflected signals, integrated over 1 s intervals, for a time sequence of NIG turning on and off. First, it was determined that in the dry air, MMW transmission or reflection was not changing to a measurable level when NIG was turning on or off. Next, with the flowing mist, a consistently higher transmission of MMW through the mist was observed when NIG was on (charged mist), compared to the case when the NIG was off (neutral mist). FIG. 12(*a*) gives a plot for a typical case of the measured MMW transmitted intensity T in arbitrary units (a.u.) as a function of time. FIG. 12(*b*) displays corresponding time readings of a charge counter placed next to the setup. The same measurements were repeated for the stationary mist case. The results for detected MMW transmitted intensity T (a.u.) are plotted in FIG. 13(*a*), and the corresponding time readings of the charge counter are displayed in FIG. 13(*b*). In order to detect back-scattered MMW, a receiver antenna and detector, coupled to a low noise 20 dB preamplifier, were placed next to the emitter antenna (bistatic geometry). The results for detected MMW reflected intensity R (a.u.) from flowing mist are plotted in FIGS. 14A and 14B, and reflected intensity measurements for stationary mist are plotted in FIGS. 15A and 15B It can be seen from the counter readings during the "off" cycles of NIG in FIGS. 12(*b*), 13(*b*), 14(*b*) and 15(*b*) that the mist does not carry a significant amount of charge. FIGS. 12(*a*) and 13(*a*) indicated that relative changes in MMW forward-scattering amplitude in response to mist charging for either flowing or stationary mist are approximately the same. Similarly, FIGS. 14(*a*) and 15(*a*) indicate that relative changes in MMW backscattering amplitude in response to ionization are approximately the same for flowing and stationary mist cases. Compared to previous studies of MMW scattering from charged cardboard cylinder, for the case of charged humid air, the amplitudes of MMW forward- and backscattering scattering signal changes are smaller, but the response time was faster. Also in the prior art, reflection and transmission signals were considered on the same order of magnitude, while in scattering from charged mist, backscattering is two orders of magnitude smaller than forward-scattering.

Example 2

Model of Millimeter-Wave Scattering from Charged Water Droplets

In general, electromagnetic scattering from random medium, such as mist, changes if the dielectric properties of the medium change in response to external stimulus. In one case, refractive index distribution function of the medium changes, i.e., average value of refractive index is the same but internal structure of the medium changes. In another case, average refractive index of the medium changes at the molecular level, i.e., dielectric polarizability of the medium changes. Both processes mentioned above can contribute to observed change in forward- and backscattering of MMW from mist in response to ionization.

In order to interpret the experimental results, the scattering and extinction cross-section of the charged and uncharged water droplets were studied. Radar scattering and extinction cross-section efficiencies of sub-micron size spherical droplets for incident MMW follow the Rayleigh law:

$$Q_{sca}(x,T)=(8/3)x^4|[\epsilon_{eff}(x,T)-1]/[\epsilon_{eff}(x,T)+2]|^2, \quad (14)$$

$$Q_{ext}(x,T)=4x1m\{[\epsilon_{eff}(x,T)-1]/[\epsilon_{eff}(x,T)+2]\}, \quad (15)$$

where $\alpha$ is the radius of the particle, $x=2\pi\alpha/\lambda$ the size parameter. Note that for a small value of the size parameter x, extinction is approximately equal to absorption. The effective dielectric function is $$\epsilon_{eff}(f,T)=\epsilon_v(f,T)+\epsilon_s(f,T) \quad (16)$$

where $\epsilon v(f,T)$ was the frequency and temperature-dependent volume dielectric constant of bulk water, and $\epsilon s(f,T)$ the frequency and temperature-dependent surface dielectric constant. A well-accepted phenomenological double Debye model of frequency and temperature-dependent dielectric properties of water was used, which was valid in the spectral range from 1 GH to 1 THz and temperature range −20 to 60° C. For laboratory conditions of T=20° C. and f=94 GHz, this model gives the value of the dielectric constant $\epsilon v=7.69+ i13.32$.

A model based on classical electrodynamics theory of scattering from a dielectric sphere with diffusion-deposited mobile surface charge provides an explanation of the example results. In this approach, scattering and extinction cross-sections are calculated for a charged Rayleigh particle with effective dielectric constant consisting of the volume dielectric function of the neutral sphere and surface dielectric function due to the oscillation of the surface charge in the presence of applied electric field. For small droplets with radius smaller than 100 nm, this model predicts increased MMW scattering from charged mist, which is qualitatively consistent with the experimental observations. It should be appreciated that this example supports the above described indirect remote sensing of radioactive gases via their charging action on atmospheric humid air.

Example 2

Diffusion Charging of Water Microdroplet

Diffusion charging of a dielectric sphere due to an external source of charges deposits a layer of surface electrons on the sphere. Electrons are confined to the single molecule-thick top-most layer of the dielectric water sphere. Existing models of aerosol diffusion charging suggest that the average number of charges may be proportional to the radius or the square of the radius of the droplet. The microscopic electrostatic model of water charging supports the linear dependence law. On the surface of a microdroplet, polar water molecules are oriented, so that oxygen atoms with excess negative charge point inward, while hydrogen atoms with excess positive charge point outward. Thus, the surface of a microdroplet can be considered as a collection of dipoles with the same orientation, where the potential difference between the layer of positive charge on the surface and the layer of negative charge just below the surface is $\Delta^\Phi=0.5$ V. (The value of $\Delta^\Phi=0.25$ V is quoted in the prior art, however, more recent results from molecular dynamics (MD) simulations suggest that $\Delta^\Phi=0.5$ V). Therefore, a water microdroplet acts as a capacitor that can accumulate a net negative surface charge. In the steady state, diffusion charging deposits a net average negative charge $$Q \approx 4\pi\epsilon_0\Delta\phi\alpha, \quad (17)$$

where $\epsilon_o$ is the free space permittivity and $\alpha$ the radius. Hence, the total average number of mobile surface electrons can be estimated as (with $\Delta\phi=0.5$ V)

$$N=Q/e \approx 2\pi\epsilon_0\alpha/e, \quad (18)$$

where e is the elementary charge.

Example 2

Surface Dielectric Constant

To calculate the response of charged droplets, a classical electrodynamics-based modified Mie model of scattering from a dielectric sphere with free surface charge was considered. Modification to conventional Mie theory is obtained via the equation of continuity of tangential magnetic fields at the boundary of the sphere $$\hat{n}\times(\vec{H}_1-\vec{H}_2)=\vec{K}, \quad (19)$$

where $\vec{K}$ is the surface current density, which can be related to the mobile surface charge as $$\vec{K}=\sigma_s\vec{E}_t=\rho_s\vec{u}, \quad (20)$$

where $\sigma_s$ is surface conductivity, Et the tangential component of the applied EM field at radial frequency $\omega$, ps surface charge density and u the tangential velocity of the charge carriers. The former can be calculated using the damped driven oscillator model. The equation of motion of mobile surface charge acted upon by the driving force $eE_t e^{-i\omega t}$ and velocity-dependent resistive force $-\gamma\mu$ is given as $$\dot{u}+\gamma u=-(e/m_e)E_t e^{-i\omega t}, \quad (21)$$

where e is the charge of electron, me the mass of electron and y=b/me the phenomenological damping constant. Note that this model assumes continuum surface charge density, which is correct for microscopic sphere. In the nanoscale regime, however, the sphere has a discrete number of surface charges, and Coulomb electron-electron repulsion may need to be accounted for. These corrections will be introduced into the model in our future work.

To obtain the Rayleigh cross-section, the modified Mie coefficients can be expanded in power series in the size parameter, and retaining the lowest order term. Then, it has been shown in that the surface dielectric function is $$\epsilon_s = -\omega_s^2/(\omega^2 + i\omega\gamma), \quad (22)$$

Here the surface plasma frequency is $$\overline{\omega}_s^2 = Ne^2/2\pi a^3 m_e \epsilon_0, \quad (23)$$

where N is the total number of mobile surface charges. Thus, $\epsilon_s$ critically depends on the values of N and y. Using the expression for N obtained in Eq. (18) provides $$\overline{\omega}_s^2 = e/m_e a^2, \quad (24)$$

so that $\overline{\omega}_s \propto 1/\alpha$

Example 2

Model of Damping Constant in Equation of Motion

Previously it has been suggested to approximate the temperature-dependent damping constant using an empirical expression $\gamma(T) \approx k_B T/h$, where $k_B$ is the Boltzmann constant and h is Planck's constant. However, this model does not relate the damping constant to the properties of the medium. To accommodate this, a classical-mechanics model of the temperature-dependent damping constant $\gamma(T)$ was developed wherein the electron is treated as a classical spherical particle that has a classical electron radius (Lorentz radius) of $$r_e = (4\pi\epsilon_0)^{-1} e^2/m_e c^2, \quad (25)$$

which has the numerical value $r_e$ $2.82 \times 10^{-15}$ m. Using the equation for linear viscous drag for a particle in water, the coefficient of resistive force in Eq. (21) is $$b = 6\pi r\eta, \quad (26)$$

where r is the Stokes radius of the particle (which for a spherical particle is the same as the radius of the particle) and $\eta$ the temperature-dependent fluid viscosity. Thus, the damping constant in Eq. (21) for the electron in water is $$\gamma(T) = b/m_e = 6\pi r_e \eta(T)/m_e \quad (27)$$

At T=20° C., the viscosity of water is $\eta = 1.0003 \times 10$-3 Pa s, so that $\gamma = 5.83 \times 1013$ rad/s.

Example 2

Computer Simulations

Figure 12A:
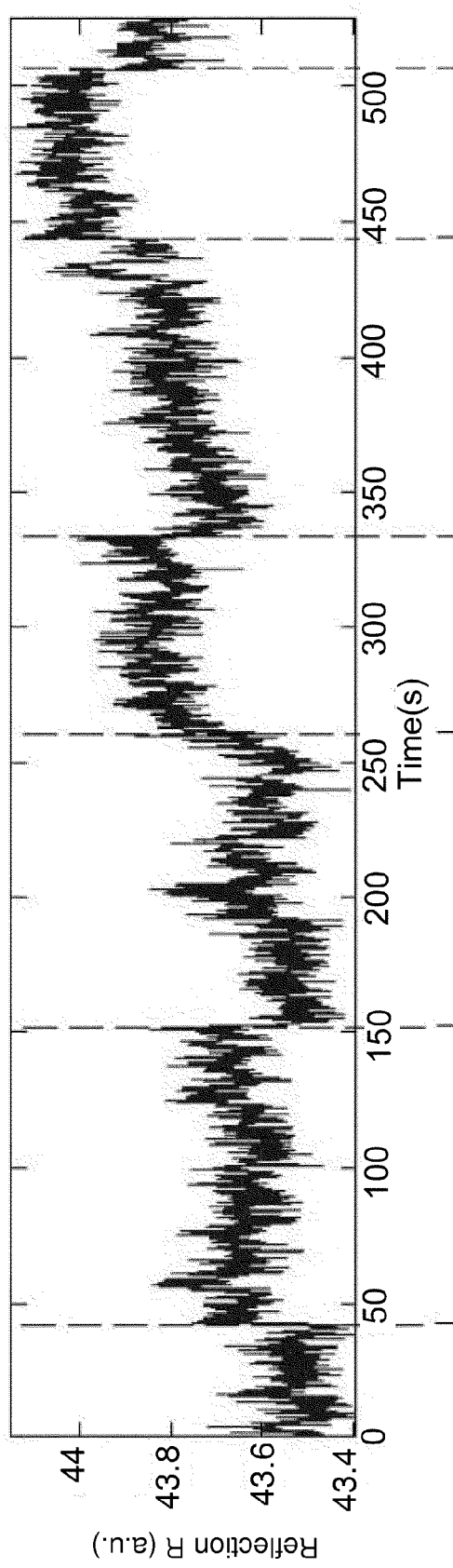
FIGS. 12A-B depict measure of a 94 Ghz MMQ backscattering from neutral and charging flowing (convective and diffusive) mist.
Figure 12B:
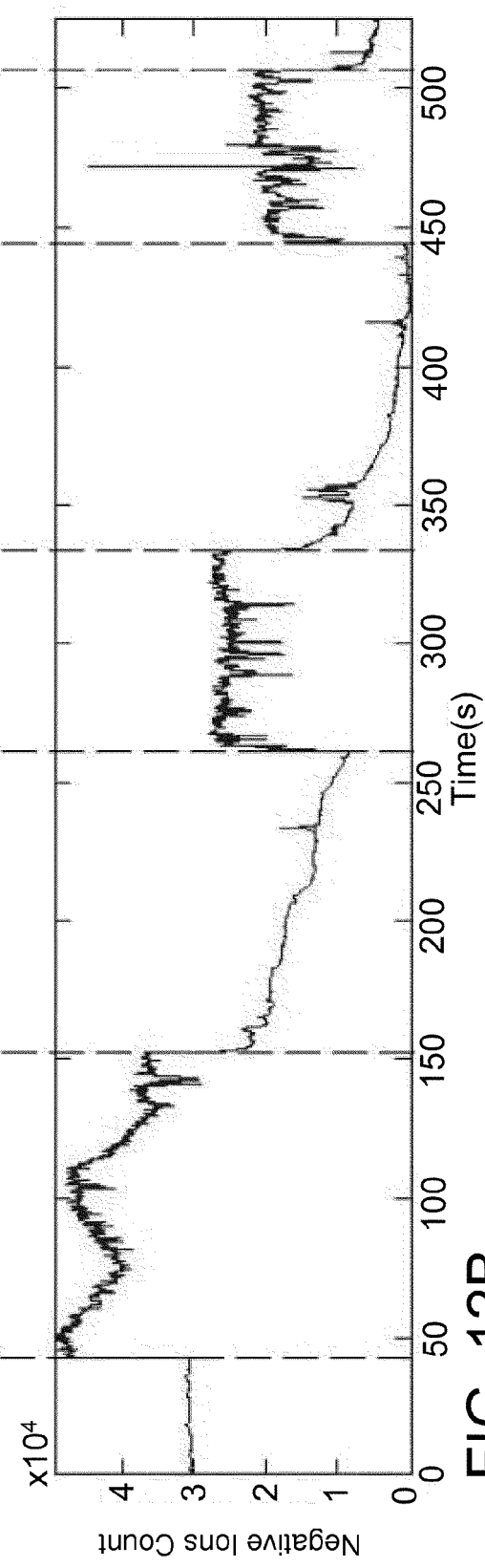
Figures 13A, 13B:
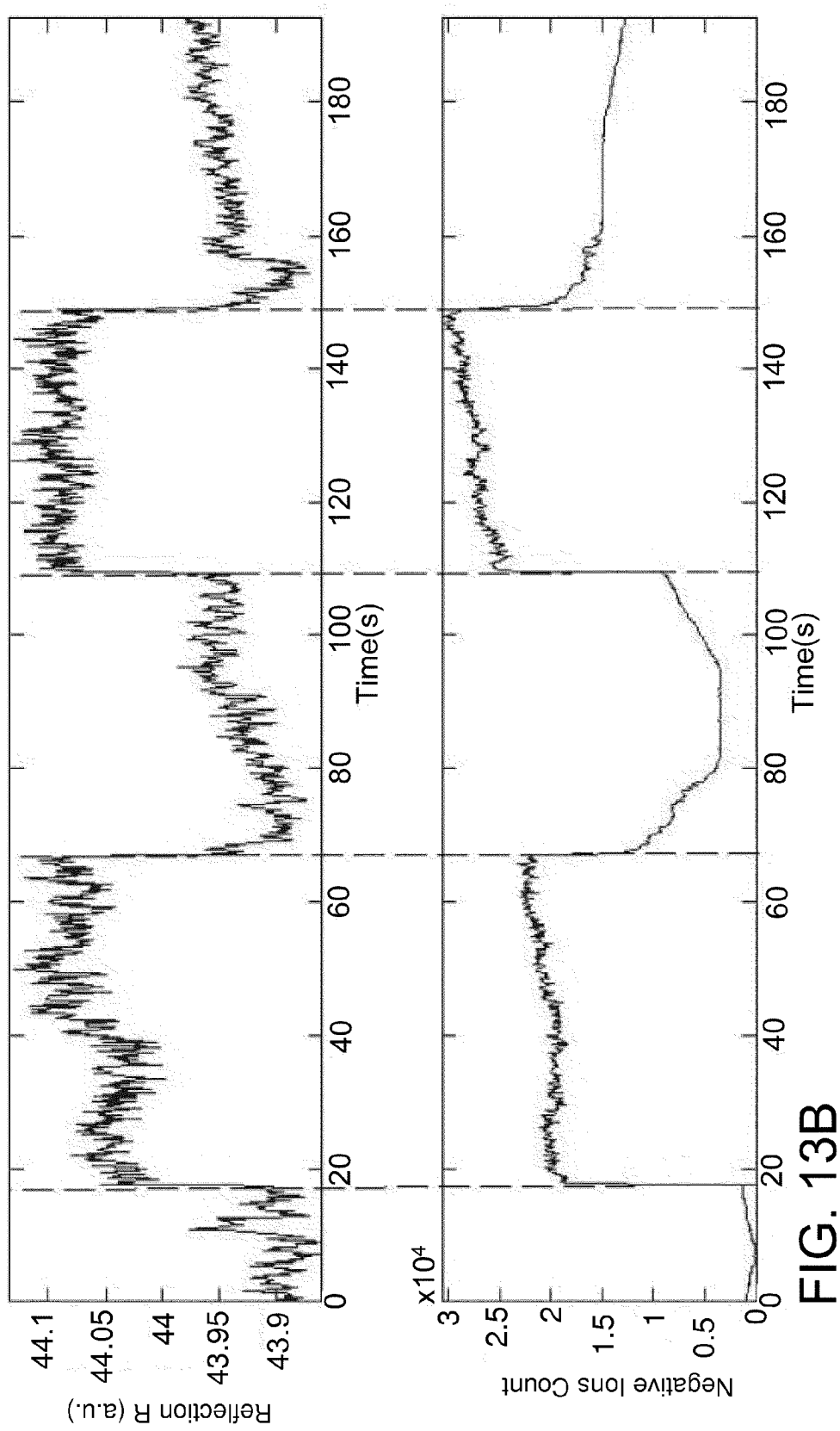
FIGS. 13A-B depict measurement of 94 GHz MMW backscattering from neutral and charged stationary (diffusive only) mist.
Figure 14:
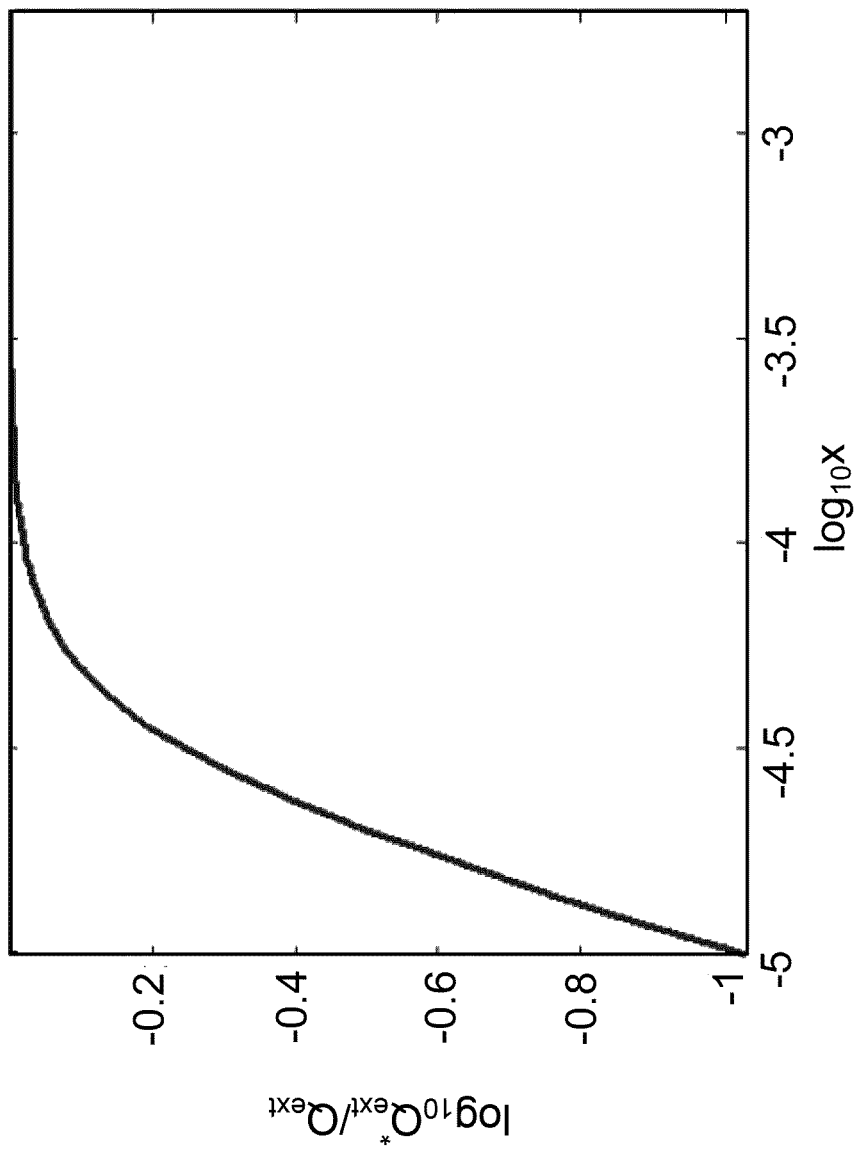
FIG. 14 is a log-log plot of computer simulations of the ratios of charged (Q*ext) to uncharged (Qext) extinction cross section efficiencies as a function of size parameter x for water droplets with radii 5 nm<a<1 µm, frequency f=94 GHz, and T=20° C.
Figure 15:
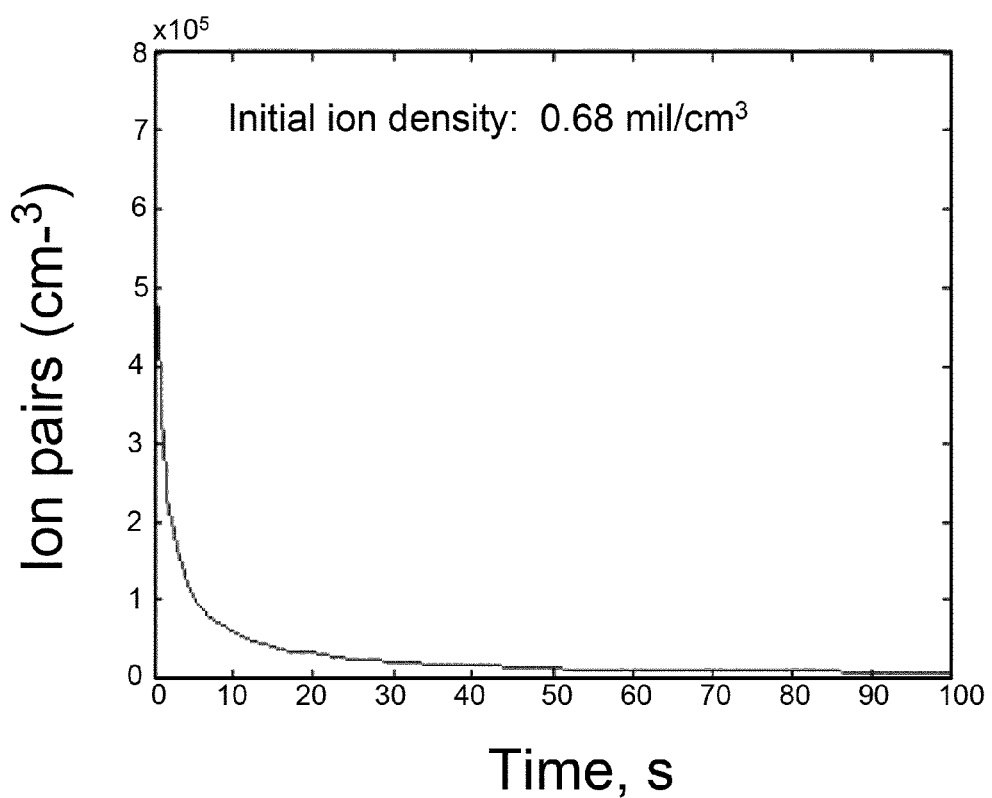
FIG. 15 is a log-log plot of computer simulations of the ratios of (Q*sca) to uncharged (Qsca) scattering coefficients as a function of size parameter x for water droplets with radii 5 nm<a<1 µm, frequency f=94 GHz, and T=20° C.
Figure 16:
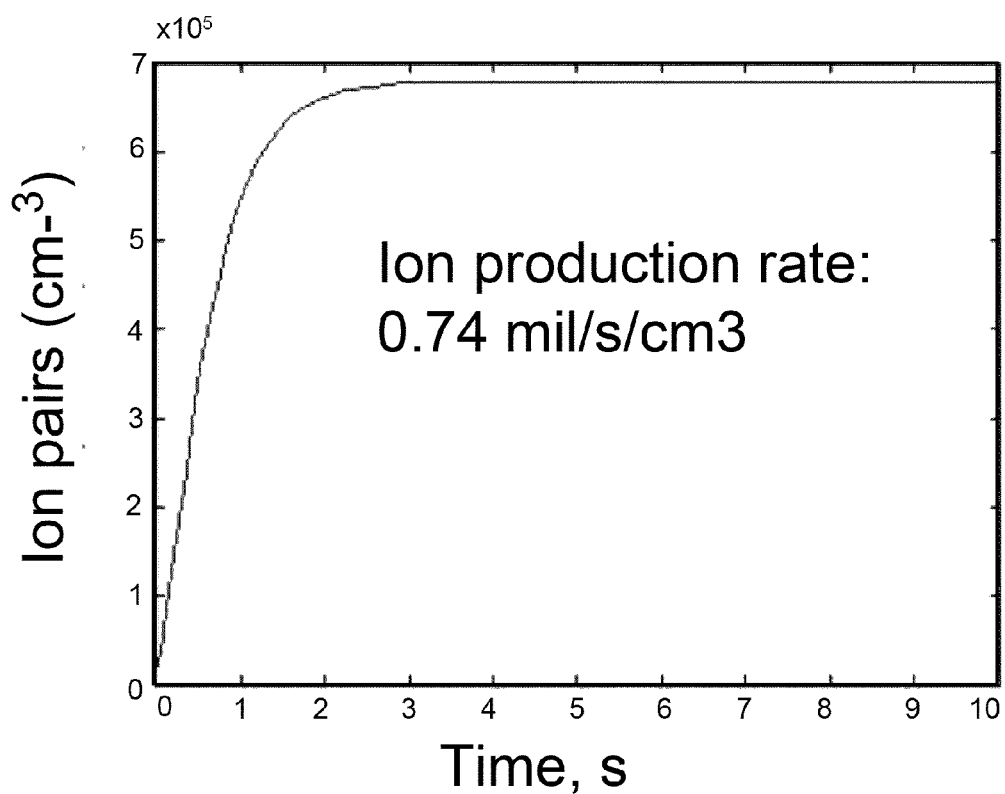
FIG. 16 is a log-linear plot of real and imaginary components of the surface dielectric function ϵs as a function of size parameter x for water droplets with radii 5 nm<a<1 µm, frequency f=94 GHz, and T=20° C.
Figure 17:
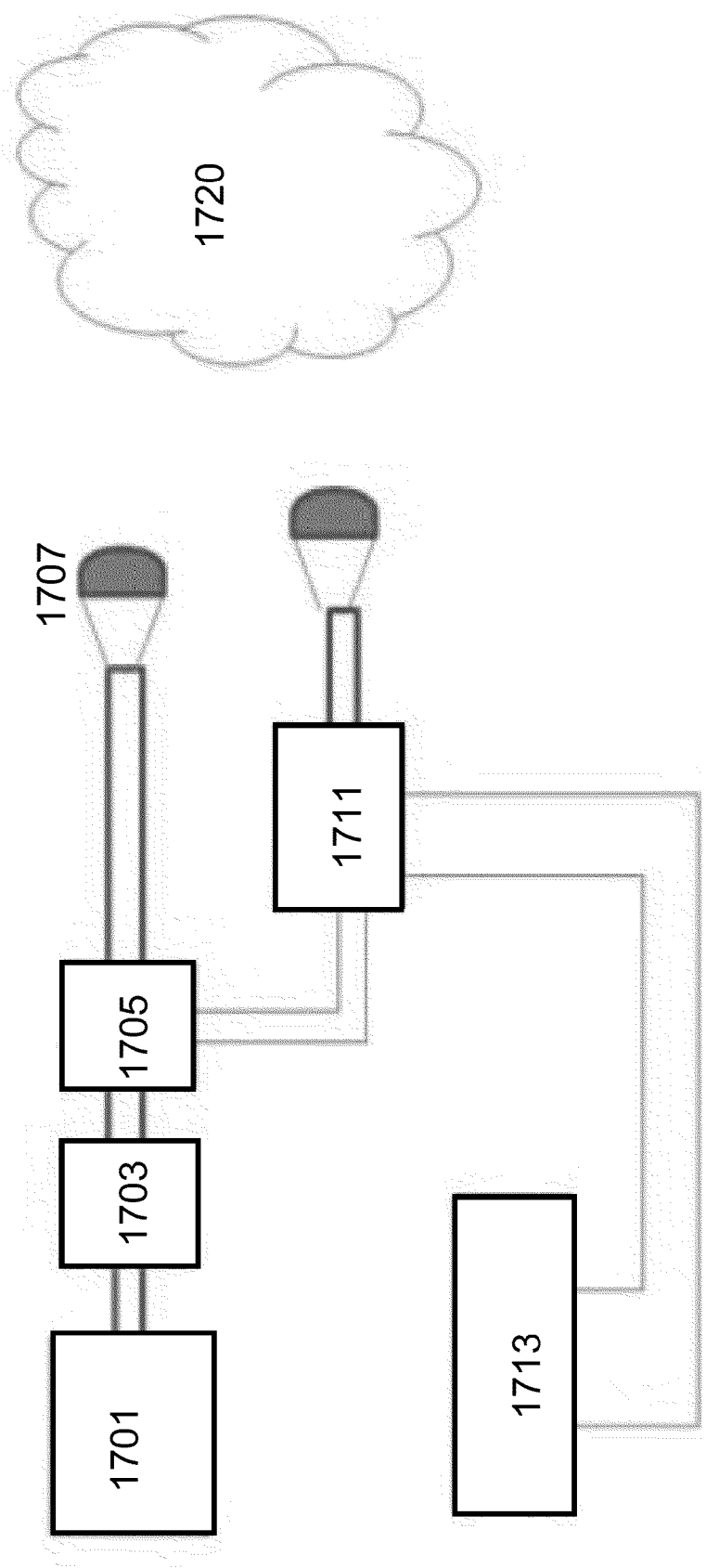
FIG. 17 illustrates an experimental setup for one embodiment of a 94 GHz millimeter wave I-Q sensor.

Using the model described above, ratios of scattering and extinction cross-sections efficiencies of charged to uncharged water droplets with radii 5 nm<a<1 µm, incident frequency f=94 GHz and T=20° C. were calculated. Log-log plot of computer simulations of the ratios of charged (Q*ext) to uncharged (Qext) extinction cross-section efficiencies as a function of the size parameter x is presented in FIG. 16. For small droplets (a<100 nm), the model predicts increased forward-scattering of MMW from charged mist, which is qualitatively consistent with experimental observations in FIGS. 12A, 12B, 13A, and 13B. Log-log plot of computer simulations of the ratios of charged (Q*sca) to uncharged (Qsca) scattering cross-section efficiencies as a function of the size parameter x is presented in FIG. 17. The model predicts increased MMW backscattering from charged mist, which is qualitatively consistent with experimental observations in FIGS. 14A, 14B, 15A, and 15B. Physical implication of these results is that for sub-micron droplets, charging increases MMW scattering and decreases MMW absorption. One can hypothesize that increased scattering is due to scattering from extra surface electrons. Absorption in water droplets is related to dissipation of energy due to vibration of dipoles in response to the oscillatory applied EM field. Thus, one of ordinary skill in the art can hypothesize that decrease in absorption due to charging may be caused by jamming of surface dipoles when extra surface charges are present. Note from Eqs. (14) and (15) that $Qsca \propto x^4$, while $Qext \propto x$. For MMW incident on mist microdroplets $x \leq 1$, so that MMW reflection signal for either charged or neutral mist is expected to be much smaller than the transmission signal for either charged or neutral mist, as shown by the relative changes between FIGS. 12A/B and 14A/B and FIGS. 13A/B and 15A/B.

Figure 18:
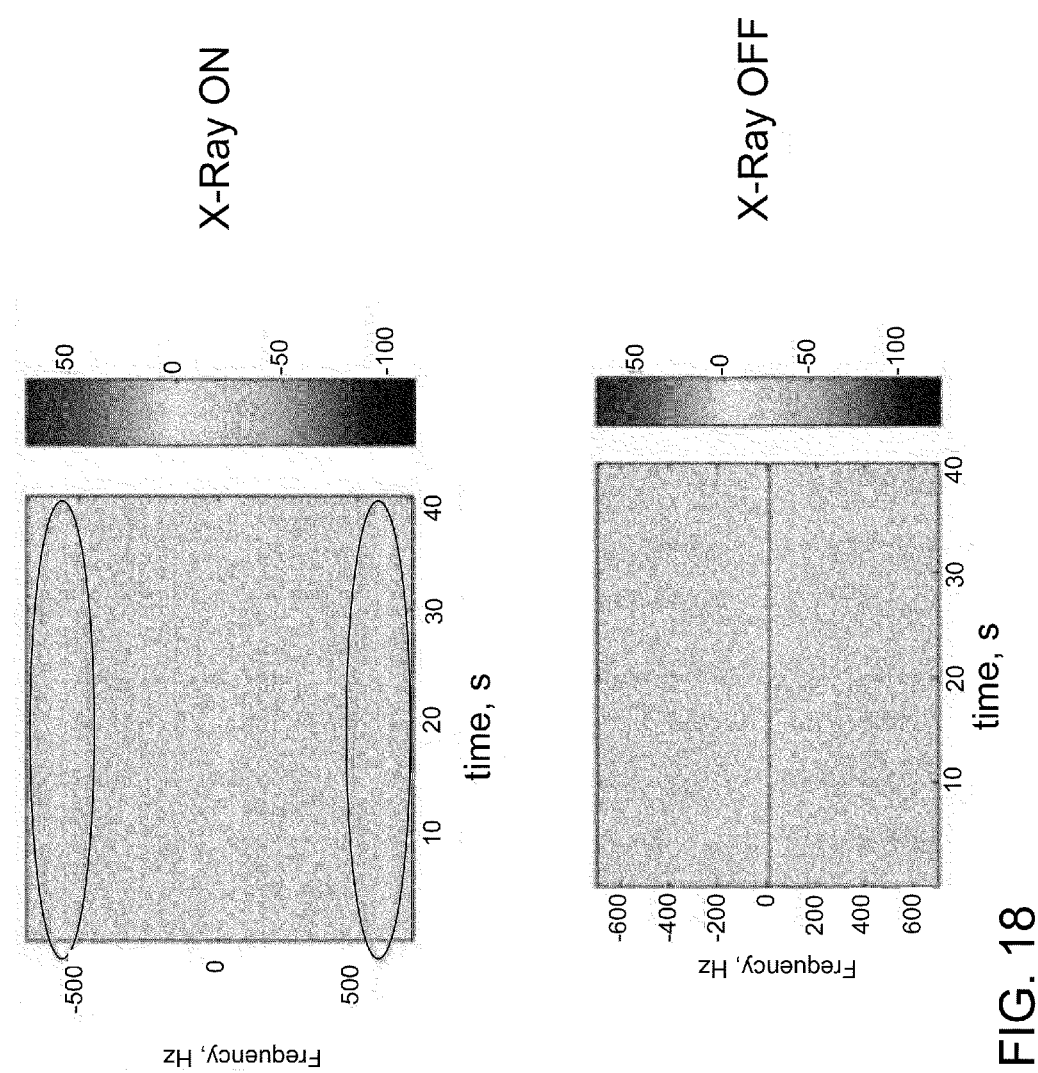

In order to gain a better understanding of the model, the real and imaginary components of the surface dielectric function $\epsilon_s$ are plotted as a function of the size parameter x for water droplets with radii 5 nm<a<1 µm, frequency f=94 GHz and T=20° C. in FIG. 18. Numerical values of the parameters used in the computer simulations are $\epsilon_v = 7.69 + i13.32$, $\omega = 5.9 \times 1011$ rad/s, $\gamma = 5.8 \times 1013$ rad/s, $\omega_s = 8.4 \times 1013$ rad/s for a=5 nm droplet, and since from Eq. (24) $\omega_s \propto 1/a$, $\omega_s = 4.2 \times 1011$ rad/s for a=1 µm droplet. From Eq. (22)

$$Re\epsilon_s = -\omega_s^2/(\omega^2 + \gamma^2) \text{ and } Im\epsilon_s = \omega_s^2 \gamma/(\omega^3 + \omega\gamma^2), \quad (28)$$

Because $\omega \ll \gamma$:

$$Re\epsilon_s \approx -\omega_s^2/\gamma^2 \text{ and } Im\epsilon_s \approx \omega_s^2/(\omega\gamma), \quad (29)$$

This explains why $Im\epsilon_s \gg Re$ for small droplets, but with an increase in size $Im\epsilon_s |0$. Note also that for small droplets $Im\epsilon_s \gg Re\epsilon_v$ and $Im\epsilon_s \gg Im\epsilon_v$. The quantity in brackets in Eqs. (14) and (15) are labeled as $\alpha$ having the numerical value $\alpha = 0.82 + i0.15$ for uncharged droplets and $$\alpha^* = [\epsilon_v + \epsilon_s - 1]/[\epsilon_v + \epsilon_s + 2], \quad (30)$$

for charged ones. One can show that for small droplets $|\alpha^*|^2 \approx 1$ and $Im\alpha^* \ll 1$, whereas $|\alpha^*|^2 = 0.82$ and $Im\alpha = 0.15$. Then, taking the appropriate ratios, one obtains that for small droplets scattering is slightly higher, while absorption is an order of magnitude smaller than the corresponding quantities for neutral droplets, as can be seen in FIGS. 13A, 13B, 14A, and 14. With increase in size, the effect of charge is diminished.

The results of the numerical experiments indicate that no significant sensitivity of the scattering and absorption cross-sections to surface charge was observable for droplets larger than approximately $\alpha = 100$ nm. For droplets smaller than approximately $\alpha = 5$ nm, our model predicts that no surface charges will be deposited. On the other hand, existing models and experimental observations indicate that most droplets produced by UA mist generators have sizes larger than 1 µm. The scattering model described herein assumes a continuum surface charge model. For a continuum, metal-like surface charge, Coulomb repulsion forces may be ignored, and drift of charges in the external field may be approximated as surface current. However, small droplets carry a discrete number of surface charges, where Coulomb repulsion cannot be ignored. Further, the examples given above ignore thermal effects. At ambient temperature, energy of thermal fluctuations $k_B T$ exceeds the energy of the driving force of applied electromagnetic field. The model damping constant presented above is an empirical one. Thus, it should be appreciated that the temperature of the water droplets may impact these results.

Example 2

Conclusion

Increased forward- and backscattering of 94 GHz millimeter-wave (MMW) from charged mist, as compared to MMW scattering from neutral mist has been observed. Comparison of the neutral and charged droplet experiments reveals increased transmission of MMW through charged mist as compared to uncharged mist. Specifically, experimental results indicate that charged mist is more transparent to millimeter waves than the uncharged mist. Note that flowing mist also produces some ionization count. Experimental results also indicate that charged droplets in humid air are more transparent to millimeter waves than the uncharged droplets. Ambient temperature mist was produced from de-ionized water with an ultrasonic atomizer (UA), and charging was accomplished with a negative ion generator (NIG) placed near the mist. The model described herein predicts increased forward-scattering and increased backscattering of MMW from small droplets, which qualitatively agrees with the observed experimental results. However, charging is predicted to affect droplets in the size range below 100 nm, while the current literature on UA-generated mist suggests that sizes of most droplets are above 1 μm.

Previously, the mechanism of scattering due to water droplets has not been completely understood. It is believed that because at room and atmospheric humidity levels, surfaces of most dielectrics are covered with thin layer of water the problem may be reduced to the understanding of charged water interaction with EM waves. It is currently believed that two plausible mechanisms may explain the microwave interaction of air ionization: (a) coherent Thomson scattering from free electrons released from ionization and (b) scattering from charged water microdroplets as they may form from ion-nucleated water clustering. The charged droplet scattering may be the case in atmospheric air as discussed above. It is believed the coherent Thomson scattering may explain the present measurements in room air.

Example 3

Field Test of Standoff Radiation Sensing Concept

A field test setup is illustrated in FIG. 17. A millimeter wave (mmW) sensor at 94 GHz measures reflected signals from radiation-induced atmospheric events at short standoff distances. A Gunn diode oscillator 1701 generates continuous-wave mmW radiation at a power level of ~60 mW. An isolator 1703 may be provided to shield input equipment. A 20 dB directional coupler 1705 transmits 99% percent of the mmW power which is radiated out by a lens antenna 1707 and directed at the target 1720. The remaining 1% of the power is fed to the reference channel of a homodyne mixer 1711. The reflected signal from the target 1720 is collected by a second lens antenna 1709 and fed to the measurement channel of the homodyne mixer 1711. A processing component, such as a computer 1713, can be used for signal analysis and processing. The target signal is converted into in-phase (I) and quadrature-phase (Q) components with respect to the reference signal. The I and Q components of the target signal may be used to measure amplitude and phase of backscattered signals from the target as well as Doppler frequency shift if the target is moving relative to the mmW beam. The Doppler frequency shift, $f_d$, of a moving target is given by:

$$f_d=2\nu_r/\lambda$$

where $\lambda$ is the carrier wavelength and $\nu_r$ is the radial velocity of the target along the beam direction.

In one test scenario utilize the above described setup, the I-Q sensor was deployed in a field test at a standoff distance of ~2m. A low energy X-Ray source was used to ionize the air in front of the I-Q sensor. The mmW backscattered signals were measured for the cases when the X-Ray source was turned on and off. As FIGS. 18*a* and 18*b* show, a Doppler frequency shift was observed around 500 Hz when the X-Ray source was on, and the shift disappeared when the X-Ray was off. This was confirmed by several measurements for different scenarios: 1) X-Ray tube pointed up toward the beam, 2) downward toward the ground, and 3) mmW beam directed away from the plume. In order to confirm the detection, a mobile radar operating on similar principle as mmW sensor, at 10 GHz, which was also deployed at the test from 100 m away. The 10 GHz radar aimed at the target from a different angle also observed this Doppler feature. The fact that both the 94 GHz and 10 GHz radars simultaneously detected this feature (after frequency scaling) adds confidence to the detection event.

The foregoing description of embodiments of the present invention has been presented for purposes of illustration and description. It is not intended to be exhaustive or to limit the present invention to the precise form disclosed, and modifications and variations are possible in light of the above teachings or may be acquired from practice of the present invention. The embodiments were chosen and described in order to explain the principles of the present invention and its practical application to enable one skilled in the art to utilize the present invention in various embodiments, and with various modifications, as are suited to the particular use contemplated.

What is claimed:

1. A remote detection system for identifying airborne radiation, comprising:

a transmitter coupled to a power source, the transmitter configured to generate an electromagnetic carrier component characterized by a wavelength on the order of a millimeter; and a transceiver configured to detect a reflected component comprising a portion of the carrier component reflected from the radiation-induced ionization of air, the transceiver adapted to obtain an amplitude and phase of the reflected component, wherein the amplitude and phase detected by the transceiver portion are indicative of the location and strength of the radiation.

2. The system of claim 1, further comprising a data acquisition system operatively connected to the transceiver, wherein the data acquisition system is adapted to digitizing the transceiver's output signal of the reflected component.

3. The system of claim 1, further comprising a display operatively connected to the transceiver, wherein the display is configured to communicate the transceiver's output signal of the reflected component.

4. The system of claim 2, further comprising a display operatively connected to the data acquisition system, wherein the display is configured to communicate the data acquisition system's digitized output signal of the reflected component.

5. The system of claim 2, further comprising a data computer operatively connected to the data acquisition system, wherein the computer processes the data acquisition system's digitized output signal of the reflected component.

6. The system of claim 3, further comprising a computer operatively connected to the transceiver, wherein the computer processes the transceiver's output signal.

7. The system of claim 4, further comprising a computer operatively connected to the DAQ system, wherein the computer processes the data acquisition system's digitized output signal of the reflected component.

8. A computerized system for locating airborne radiation, the system comprising:
- a transmitter coupled to a power source, the transmitter configured to generate an electromagnetic carrier component characterized by a wavelength on the order of a millimeter;
- a transceiver configured to detect a reflected component comprising a portion of the carrier component reflected from the radiation-induced ionization of air, the transceiver adapted to obtain an amplitude and phase of the reflected component;
- a processing unit; and
- a storage device coupled to the processing unit having stored therein computer readable code configured to:
- receive information regarding the detected reflected component, the information including at least amplitude and phase;
- analyze the received reflected component information;
- determine the location and strength of the airborne radiation.

9. The computerized system of claim 8, further comprising a data acquisition system operatively connected to the transceiver, wherein the data acquisition system is adapted to digitizing the transceiver's output signal of the reflected component.

10. The computerized system of claim 8, further comprising a display operatively connected to the transceiver, wherein the display is configured to communicate the transceiver's output signal of the reflected component.

11. The computerized system of claim 10, further comprising a display operatively connected to the data acquisition system, wherein the display is configured to communicate the data acquisition system's digitized output signal of the reflected component.

12. The computerized system of claim 9, further comprising a data computer operatively connected to the data acquisition system, wherein the computer processes the data acquisition system's digitized output signal of the reflected component.

13. The computerized system of claim 10, further comprising a computer operatively connected to the transceiver, wherein the computer processes the transceiver's output signal.

14. The computerized system of claim 11, further comprising a computer operatively connected to the DAQ system, wherein the computer processes the data acquisition system's digitized output signal of the reflected component.

15. A method for remotely detecting airborne radiation, comprising the steps of:
- providing a remote detection system for identifying airborne radiation;
- emitting an electromagnetic carrier component characterized by a wavelength on the order of a millimeter, the emitted electromagnetic carrier component directed at an area of interest remote from the remote detection system;
- interacting the electromagnetic carrier component with a radioactive plume in the area of interest;
- receiving a portion of the electromagnetic carrier component reflected back to the remote detection system by the charged water droplets, the received electromagnetic carrier having a different amplitude and phase than the emitted electromagnetic carrier component; and
- analyzing the received electromagnetic carrier to determine the location and strength of radiation in the area of interest, wherein the amplitude and phase detected by the transceiver portion are indicative of the location and strength of the radiation.

16. The method of claim 15, wherein the electromagnetic carrier component interacts with charged water droplets in the area of interest.

17. The method of claim 15, further comprising converting the received portion of the electromagnetic carrier into in-phase (I) and quadrature-phase (Q) components with respect to the emitted electromagnetic carrier.

18. The method of claim 17, further comprising determining if the radioactive plume is moving relative to the remote detection system.

19. The method of claim 17, wherein the Doppler frequency shift, $f_d$, of the radioactive plume is given by:

$$f_d = 2v_r/\lambda$$

where $\lambda$ is the carrier wavelength and $v_r$ is the radial velocity of the radioactive plume along the emitted electromagnetic carrier component direction.

* * * * *